United States Patent
Spatola et al.

[11] Patent Number: 6,008,058
[45] Date of Patent: Dec. 28, 1999

[54] CYCLIC PEPTIDE MIXTURES VIA SIDE CHAIN OR BACKBONE ATTACHMENT AND SOLID PHASE SYNTHESIS

[75] Inventors: Arno F. Spatola, Louisville; Krzysztof Darlak, Fisherville; James Jun Wen; Peteris Romanovskis, both of Louisville, all of Ky.

[73] Assignee: University of Louisville, Louisville, Ky.

[21] Appl. No.: 08/423,091

[22] Filed: Apr. 18, 1995

Related U.S. Application Data

[63] Continuation-in-part of application No. 08/079,019, Jun. 18, 1993, abandoned.

[51] Int. Cl.$^6$ .................... G01N 33/543; C07C 5/12; C07C 7/00; C07C 17/00
[52] U.S. Cl. .................... 436/518; 436/524; 436/526; 436/528; 530/317; 530/333; 530/334
[58] Field of Search .................... 436/518, 524, 436/526, 528; 530/317, 318, 333, 334, 335, 337, 341

[56] References Cited

U.S. PATENT DOCUMENTS

| | | |
|---|---|---|
| 4,659,691 | 4/1987 | Veber et al. . |
| 4,663,309 | 5/1987 | Kaiser et al. . |
| 4,757,048 | 7/1988 | Lewicki et al. . |
| 4,778,784 | 10/1988 | Dreesman et al. . |
| 4,786,684 | 11/1988 | Glass . |
| 4,914,188 | 4/1990 | Dumònt et al. . |
| 4,959,352 | 9/1990 | Felix et al. . |
| 5,010,175 | 4/1991 | Rutter et al. . |
| 5,043,322 | 8/1991 | Rivier et al. . |
| 5,064,939 | 11/1991 | Rivier et al. . |
| 5,084,442 | 1/1992 | Felix et al. . |
| 5,120,859 | 6/1992 | Webb . |
| 5,134,123 | 7/1992 | Branca et al. . |
| 5,143,854 | 9/1992 | Pirrung et al. . |
| 5,149,778 | 9/1992 | Adams et al. . |
| 5,164,481 | 11/1992 | Lacroix et al. . |
| 5,166,394 | 11/1992 | Breipohl . |
| 5,169,862 | 12/1992 | Burke, Jr. et al. . |
| 5,175,144 | 12/1992 | Basava et al. . |
| 5,182,263 | 1/1993 | Danno et al. . |
| 5,182,366 | 1/1993 | Huebner et al. . |
| 5,186,824 | 2/1993 | Anderson et al. . |
| 5,194,392 | 3/1993 | Geysen . |

OTHER PUBLICATIONS

"Simultaneous Multiple Synthesis and Selective Conjugation of Cyclized Peptides Derived From A Surface Loop of a Meningococcal Class 1 Outer Membrane Protein", by H.F. Bruggie, in *Int. J. Peptide Protein Res.*, vol. 43, pp. 166–172, 1994.

"Multiple Release of Equimolar Amounts of Peptides from a Polymeric Carrier Using Orthogonal Linkage–Cleavage Chemistry" by M. Lebl, in *Int. J. Peptide Protein Res.* vol. 41, pp. 201–203, 1993.

(List continued on next page.)

*Primary Examiner*—Ponnathapura Achutamurthy
*Attorney, Agent, or Firm*—David W. Carrithers

[57] ABSTRACT

A method of preparing cyclic peptide mixtures via side chain or backbone and solid phase synthesis. The cyclic peptide mixtures form libraries that are useful for screening purposes featuring the attachment of an amino acid to a solid support through its side chain or backbone in order to mimic solution cyclization procedures with linear peptides. In the preferred embodiment, Boc chemistry is used for peptide synthesis, wherein the initial attachment of a trifunctional amino acid is by the aspartyl side chain (with OFm for alpha-carboxyl protection). Cyclization is performed using uronium reagents with racemization suppressant, and a strong acid (HF) is used for deprotection and cleavage. The strategy has been used for the preparation of a series of cyclic peptide mixtures. The procedure is expandable to include at least twenty different amino acids at each position (except the resin linked position where most attachments are by Asp, Lys, Glu, or Orn). The cyclic peptide mixtures vary in ring size from about four to about twelve residues.

24 Claims, 7 Drawing Sheets

1) Remove P'
2) Add P'—AA$_n$
3) Remove P' add P'—AA(SP)$_{n-2}$
4) Repeat steps until synthesis complete solid support 1) Remove P' and P"
2) Cyclize (on solid support)
3) Remove any remaining side chain protecting groups (SP) and cleave from solid support
4) Bioassay or antibody affinity procedures AA = individual amino acid or mixture of amino acids
SP = side chain protecting groups of appropriate functionality

OTHER PUBLICATIONS

Meldal, "Multiple Column Peptide Synthesis: Development and Application", *Peptides*, pp. 61–62, 1992.

Lebl and Hruby, "synthesis of Cyclic Peptides by Solid Phase Methodology", *Tetrahedron Letters*, vol. 25, No. 20, pp. 2067–2068, 1984.

Arno F. Spatola, Krzysztof Darlak, and Peteris Romanovskis Cyclic Peptide Libraries: Reducing Epimerization in Medium Sized Rings During Solid Phase Synthesis:, *Tetrahedron Letters*, pp. 37, 591–594, (1996).

O'Neil, Hoess, Jackson, Ramachandran, Mousa, and Degrado, "Identification of Novel Peptide Antagonists for GPIIb/IIIa From a Conformationally Constrained Phage Peptide Library", *Proteins*, vol. 14, No. 4, pp. 509–515, 1992.

"Biologically Active Conformations of Thymopentin" by Heavner, G.A. et al., *Int. J. Peptide Protein Res.* 37, 1991, 198–209.

"Solid Phase Synthesis of a Cyclic peptide Using Fmoc Chemistry", by J.S. McMurray, in *Tetrahedron Letters*, vol. 32, No. 52, pp. 7679–7682, 1991.

"Macrocyclization Equilibria of Polypeptides" by M. Mutter in *Journal of American Chemical society*, vol. 99, No. 25, Dec. 7, 1977.

Spanevello et al: Synthesis of Novel High Potent Cyclic–Hexapeptide Analogues of Somatostatin. Potential Application of Orthogonal Protection for Affinity Chromatography. Tetrahedron Letters, vol. 32, 1991, pp. 4675–4678.

Trzeciak et al: Synthesis of 'Head–to–Tail' Cyclized Peptides on Solid Supports by Fmoc Chemistry. Tetrahedron Letters, vol. 33, 1992, pp. 4557–4560.

Jian J. Chen, Lynn M. Teesch, and Arno F. Spatola, "Using Cyclic Peptide Mixtures as Probes for Metal Ion Host–Guest Interactions", *Letters in Peptide Science*, 3 17–24 (1996); and.

Birkett et al., "Determination of Enzyme Specificity in a Complex Mixture of Peptide Substrates by N–Terminal Sequence Analysis," *Analytical Biochemistry*, v. 196, pp. 137–143 (1991).

Kerr et al., "Encoded Combinatorial Peptide Libraries Containing Non–Natural Amino Acids," *Journal of American Chemical Society*, v. 155, pp. 2529–2531 (1993).

Felix et al., "Applications of BOP reagent in solid phase synthesis," *Int. J. Peptide Protein Res.*, v. 31, pp. 231–238 (1988).

Houghten et al., "The Use of Sythetic Peptide Combinatorial Libraries for the Identification of Bioactive Peptides," *Peptide Research* v. 5 #6, pp. 351–358 (1992).

Jung and Beck–Sickinger, "Multiple Peptide Synthesis Methods and their applications," *Angewandte Chemie International Edition in English*, v. 3 #4, pp. 367–486 (1992).

Scott, "Discovering peptide ligands using epitope libraries" *Tibs*, v. 17 pp. 240–245 (1992).

Houghten et al., "Generation and use of synthetic peptide combinatorial libraries for basic research and drug discovery," *Nature*, v. 354, pp. 84–86 (1991).

Lam et al., "A new type of synthetic peptide library for identifying ligand–binding activity", *Nature*, v. 354, pp. 82–84 (1991).

Furka et al., "General Method for rapid synthesis of multi-–component peptide mixtures," *Im. J. Peptide Protein Res.*, v. 37 pp. 487–493 (1991).

Frank, "Spot Synthesis: Positionally addressable, parallel chemical synthesis on membrane supports," *Peptides*, pp. 59–62 (1992).

Sebestyen et al., "Effieciency and limitations of the 'portioning–mixing' peptide synthesis," *Peptides*, pp. 63–69 (1992).

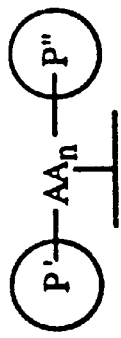 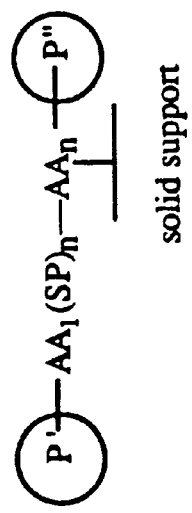

1) Remove P'
2) Add P'—AA$_n$
3) Remove P' add P'—AA(SP)$_{n-2}$
4) Repeat steps until synthesis complete solid support 1) Remove P' and P"
2) Cyclize (on solid support)
3) Remove any remaining side chain protecting groups (SP) and cleave from solid support
4) Bioassay or antibody affinity procedures AA = individual amino acid or mixture of amino acids
SP = side chain protecting groups of appropriate functionality

FIG. 1

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 5 amino acid residues
      (B) TYPE: amino acids
      (C) STRANDEDNESS: single
      (D) TOPOLOGY: circular (ii) MOLECULE TYPE: Cyclic Peptide (iii) HYPOTHETICAL:

(iv) ANTI-SENSE:

(v) FRAGMENT TYPE:

```
       (vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:   Xaa in Location 1 is Ala Tyr
                Trp or Phe
            (Locations 2 and 4 are "D" amino acids)

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 1:

Xaa Leu Val Pro Asp
 1               5

(2) INFORMATION FOR SEQ ID NO: 2:

(i) SEQUENCE CHARACTERISTICS:
            (A) LENGTH: 5 amino acid residues
            (B) TYPE: amino acids
            (C) STRANDEDNESS: single
            (D) TOPOLOGY: circular (ii) MOLECULE TYPE: Cyclic Peptide (iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
```

```
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:  Xaa in Location 1 is
                Phe Tyr Trp or Nal
            (Locations 2 and 4 are "D" amino acids)
                Xaa in Location 3 is Gly, Ala, Val or Leu (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 2:

Xaa Leu Xaa Pro Asp
 1           5

(2) INFORMATION FOR SEQ ID NO: 3:

(i) SEQUENCE CHARACTERISTICS:
            (A) LENGTH: 5 amino acid residues
            (B) TYPE: amino acid
            (C) STRANDEDNESS: single
            (D) TOPOLOGY: circular (ii) MOLECULE TYPE: Cyclic Peptide (iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:  Xaa in Location 1 is
                Ala Phe Tyr Ile His or Gly
                Xaa in Location 2 is Lys Ala Thr Phe Glu or Pro
                Xaa in Location 3 is Arg Gly Trp Phe Met or Glu
                Xaa in Location 4 is Gly Tyr Val Leu Ser or Glu (x) PUBLICATION INFORMATION:
            (A) AUTHORS:
```

```
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 3:

Xaa Xaa Xaa Xaa Asp
1               5

(2) INFORMATION FOR SEQ ID NO: 4:

(i) SEQUENCE CHARACTERISTICS:
            (A) LENGTH: 6 amino acid residues
            (B) TYPE: amino acid
            (C) STRANDEDNESS: single
            (D) TOPOLOGY: circular (ii) MOLECULE TYPE: Cyclic Peptide (iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:  Xaa in Location 4 is
                Arg Gly Trp or Phe
                    Xaa in Location 5 is Gly Tyr Val or Leu (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 4:

Ala Gln Phe Xaa Xaa Asp
1               5
```

(2) INFORMATION FOR SEQ ID NO: 5:

(i) SEQUENCE CHARACTERISTICS:
        (A) LENGTH: 6 amino acid residues
        (B) TYPE: amino acid
        (C) STRANDEDNESS: single
        (D) TOPOLOGY: circular (ii) MOLECULE TYPE: Cyclic Peptide (iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION: Xaa in Location 4 is
            Arg Gly Trp or Phe
            Xaa in Location 5 is Gly Tyr Val or Leu
            Location 1 is D-Ala (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 5:

Ala Gln Phe Xaa Xaa Asp
1              5

(2) INFORMATION FOR SEQ ID NO:6:

(i) SEQUENCE CHARACTERISTICS:
        (A) LENGTH: 6 amino acid residues
        (B) TYPE: amino acid
        (C) STRANDEDNESS: single
        (D) TOPOLOGY: circular (ii) MOLECULE TYPE:

(iii) HYPOTHETICAL:

(iv) ANTI-SENSE:

(v) FRAGMENT TYPE:

```
        (vi) ORIGINAL SOURCE:
             (A) ORGANISM:
             (B) STRAIN:
             (C) INDIVIDUAL ISOLATE:
             (D) DEVELOPMENTAL STAGE:
             (E) HAPLOTYPE:
             (F) TISSUE TYPE:
             (G) CELL TYPE:
             (H) CELL LINE:
             (D) ORGANELLE:

(vii) IMMEDIATE SOURCE:
             (A) LIBRARY:
             (B) CLONE:

(viii) POSITION IN GENOME:
             (A) CHROMOSOME/SEGMENT:
             (B) MAP POSITION:
             (C) UNITS:

(ix) FEATURE:
             (A) NAME/KEY:
             (B) LOCATION:
             (C) IDENTIFICATION METHOD:
             (D) OTHER INFORMATION:  Xaa in Location 4 is
                 Arg Gly Trp or Phe
                 Xaa in Location 5 is Gly Tyr Val or Leu (x) PUBLICATION INFORMATION:
             (A) AUTHORS:
             (B) TITLE:
             (C) JOURNAL:
             (D) VOLUME:
             (E) ISSUE:
             (F) PAGES:
             (G) DATE:
             (H) DOCUMENT NUMBER:
             (I) FILING DATE:
             (J) PUBLICATION DATE:
             (K) RELEVANT RESIDUES IN SEQ ID NO:

(xi) SEQUENCE DESCRIPTION: SEQ ID NO: 6:

Pro Gln Phe Xaa Xaa Asp
 1               5

(2) INFORMATION FOR SEQ ID NO: 7:

(i) SEQUENCE CHARACTERISTICS:
             (A) LENGTH: 6 amino acid residues
             (B) TYPE: amino acid
             (C) STRANDEDNESS: single
             (D) TOPOLOGY: circular (ii) MOLECULE TYPE: Cyclic Peptide (iii) HYPOTHETICAL:

(iv) ANTI-SENSE:

(v) FRAGMENT TYPE:

(vi) ORIGINAL SOURCE:
             (A) ORGANISM:
             (B) STRAIN:
             (C) INDIVIDUAL ISOLATE:
             (D) DEVELOPMENTAL STAGE:
             (E) HAPLOTYPE:
             (F) TISSUE TYPE:
             (G) CELL TYPE:
             (H) CELL LINE:
             (I) ORGANELLE:

(vii) IMMEDIATE SOURCE:
             (A) LIBRARY:
             (B) CLONE:

(viii) POSITION IN GENOME:
             (A) CHROMOSOME/SEGMENT:
```

```
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION: Xaa in Location 4 is
                Arg Gly Trp or Phe
                Xaa in Location 5 is Gly Tyr Val or Leu
                Location 1 is D-Pro (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 7:

Pro Gln Phe Xaa Xaa Asp
 1               5

(2) INFORMATION FOR SEQ ID NO: 8:

(i) SEQUENCE CHARACTERISTICS:
            (A) LENGTH: 7 amino acid residues
            (B) TYPE: amino acid
            (C) STRANDEDNESS: single
            (D) TOPOLOGY: circular (ii) MOLECULE TYPE: Cyclic Peptide (iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:  Xaa in Location 2 is
                Leu, Phe, Trp, Ala
                Xaa in Location 3 is Ala, D-Ala, Phe, D-Phe
                Xaa in Location 4 is Ile, Ala, D-Ala, Val
                Xaa in Location 6 is Phe, D-Phe, Ala, D-Ala (x) PUBLICATION INFORMATION:
            (A) AUTHORS:
            (B) TITLE:
```

```
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 8:

Tyr Xaa Xaa Xaa Pro Xaa Asn
1               5

(2) INFORMATION FOR SEQ ID NO: 9:

(i) SEQUENCE CHARACTERISTICS:
            (A) LENGTH: 7 amino acid residues
            (B) TYPE: amino acid
            (C) STRANDEDNESS: single
            (D) TOPOLOGY: circular (ii) MOLECULE TYPE: Cyclic Peptide (iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:   Xaa in Location 2 is
                Leu, Phe, Trp, Ala
                Xaa in Location 3 is Ala D-Ala, Phe, D-Phe
                Xaa in Location 4 is Ile, Ala, D-Ala, Val
                Xaa in Location 6 is Phe, D-Phe, Ala, D-Ala
                Location 1 is D-Tyr (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 9:

Tyr Xaa Xaa Xaa Pro Xaa Asn
1               5
```

```
(2) INFORMATION FOR SEQ ID NO: 10:

(i) SEQUENCE CHARACTERISTICS:
        (A) LENGTH: 7 amino acid residues
        (B) TYPE: amino acid
        (C) STRANDEDNESS: single
        (D) TOPOLOGY: circular (ii) MOLECULE TYPE: Cyclic Peptide (iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:  Xaa in Location 2 is
             Leu, Phe, Trp, Ala
             Xaa in Location 3 is Ala, D-Ala, Phe, D-Phe
             Xaa in Location 4 is Ile, Ala, D-Ala, Val
             Xaa in Location 6 is Phe, D-Phe, Ala, D-Ala (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 10:

Ser Xaa Xaa Xaa Pro Xaa Asn
1               5

(2) INFORMATION FOR SEQ ID NO: 11:

(i) SEQUENCE CHARACTERISTICS:
        (A) LENGTH: 7 amino acid residues
        (B) TYPE: amino acid
        (C) STRANDEDNESS: single
        (D) TOPOLOGY: circular (ii) MOLECULE TYPE: Cyclic peptide (iii) HYPOTHETICAL:

(iv) ANTI-SENSE:
```

```
            (v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:   Xaa in Location 2 is
                    Leu, Phe, Trp, Ala
                    Xaa in Location 3 is Ala, D-Ala, Phe, D-Phe
                    Xaa in Location 4 is Ile, Ala, D-Ala, Val
                    Xaa in Location 6 is Phe, D-Phe, Ala, D-Ala
                    Location 1 is D-Ser (x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO: 11:

Ser Xaa Xaa Xaa Pro Xaa Asn
1               5

(2) INFORMATION FOR SEQ ID NO: 12:

(i) SEQUENCE CHARACTERISTICS:
                (A) LENGTH: 7 amino acid residues
                (B) TYPE: amino acid
                (C) STRANDEDNESS: single
                (D) TOPOLOGY: circular (ii) MOLECULE TYPE: Cyclic Peptide (iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:
```

```
        (vii) IMMEDIATE SOURCE:
              (A) LIBRARY:
              (B) CLONE:

(viii) POSITION IN GENOME:
              (A) CHROMOSOME/SEGMENT:
              (B) MAP POSITION:
              (C) UNITS:

(ix) FEATURE:
              (A) NAME/KEY:
              (B) LOCATION:
              (C) IDENTIFICATION METHOD:
              (D) OTHER INFORMATION:  Xaa in Location 2 is
                    Leu, Phe, Trp, Ala
                    Xaa in Location 3 is Ala, D-Ala, Phe, D-Phe
                    Xaa in Location 4 is Ile, Ala, D-Ala, Val
                    Xaa in Location 6 is Phe, D-Phe, Ala, D-Ala (x) PUBLICATION INFORMATION:
              (A) AUTHORS:
              (B) TITLE:
              (C) JOURNAL:
              (D) VOLUME:
              (E) ISSUE:
              (F) PAGES:
              (G) DATE:
              (H) DOCUMENT NUMBER:
              (I) FILING DATE:
              (J) PUBLICATION DATE:
              (K) RELEVANT RESIDUES IN SEQ ID NO:

(xi) SEQUENCE DESCRIPTION: SEQ ID NO: 12:

Thr Xaa Xaa Xaa Pro Xaa Asn
 1               5

(2) INFORMATION FOR SEQ ID NO: 13:

(i) SEQUENCE CHARACTERISTICS:
              (A) LENGTH: 7 amino acid residues
              (B) TYPE: amino acid
              (C) STRANDEDNESS: single
              (D) TOPOLOGY: circular (ii) MOLECULE TYPE: Cyclic Peptide (iii) HYPOTHETICAL:

(iv) ANTI-SENSE:

(v) FRAGMENT TYPE:

(vi) ORIGINAL SOURCE:
              (A) ORGANISM:
              (B) STRAIN:
              (C) INDIVIDUAL ISOLATE:
              (D) DEVELOPMENTAL STAGE:
              (E) HAPLOTYPE:
              (F) TISSUE TYPE:
              (G) CELL TYPE:
              (H) CELL LINE:
              (I) ORGANELLE:

(vii) IMMEDIATE SOURCE:
              (A) LIBRARY:
              (B) CLONE:

(viii) POSITION IN GENOME:
              (A) CHROMOSOME/SEGMENT:
              (B) MAP POSITION:
              (C) UNITS:

(ix) FEATURE:
              (A) NAME/KEY:
              (B) LOCATION:
              (C) IDENTIFICATION METHOD:
              (D) OTHER INFORMATION:  Xaa in Location 2 is
                    Leu, Phe, Trp, Ala
```

```
            Xaa in Location 3 is Ala, D-Ala, Phe, D-Phe
            Xaa in Location 4 is Ile, Ala, D-Ala, Val
            Xaa in Location 6 is Phe, D-Phe, Ala, D-Ala
            Location 1 is D-Thr (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 13:

Thr Xaa Xaa Xaa Pro Xaa Asn
1               5
```

CYCLIC PEPTIDE MIXTURES VIA SIDE CHAIN OR BACKBONE ATTACHMENT AND SOLID PHASE SYNTHESIS

CIP notice: This is a continuation in part of patent application Ser. No. 08/079,019 filed on Jun. 18, 1993 now abandoned.

The invention described herein was supported by NIH GM-33376

BACKGROUND OF THE INVENTION

The instant invention relates to a method for preparing mixtures of cyclic peptides using novel solid phase methods such that a variety of products are prepared, in groups, possessing diversity in size, length, (molecular weight), and structural elements. These are then analyzed for the ability to bind specifically to an antibody, receptor, or other ligate. Such a collection may provide a ligand library containing specific ligands for any ligate even though there are a greater number of conformations available to any one sequence. A peptide library containing known and random peptide sequences can be easily surveyed for strong ligands and provides a powerful new tool for the cell biologist for studying molecular recognition. Moreover, the present invitation provides a means for displaying the peptides in these libraries on a selected surface allowing the library to be surveyed without the need to pick through peptides one at a time. Such a tool provides a means of recognizing a new class of agonists, antagonists, enzyme inhibitors, virus blockers, vaccine development, and other pharmaceuticals.

The use of peptide libraries for generating structurally diverse compounds is impressive. Using only the 20 common amino acids, one can readily generate 400 dipeptides or $6.4 \times 10^6$ hexapeptides. (See Table I following).

TABLE I

Listing of Theoretical Numbers of Cyclic Peptides of N Ring Size Using 20 Common Amino Acids.

| Ring Size (N) | Multiples | Number of peptides* |
|---|---|---|
| 3 | 20 × 20 × 20 | 8,000 |
| 4 | 20 × 20 × 20 × 20 | 160,000 |
| 5 | 20 × 20 × 20 × 20 × 20 | 3,200,000 |
| 6 | 20 × 20 × 20 × 20 × 20 × 20 | 64,000,000 |

*Does not include redundant peptides due to summary (e.g., cyclo(Ala-Ala-Ala).

With nineteen other D amino acids, the number rises to over 1500 dipeptides and over 3.5 billion linear hexapeptides; the magnitude of this latter number can best be realized by calculating that if only 1 milligram of each peptide were present, the weight of the 6.5 billion peptides would nevertheless exceed three tons.

One of the first practical application of multiple peptide synthesis is attributed to Geysen, H. M., et al., *Proc. Natl Acad. Sci. U.S.A.*, 81, 3998–4002, (1984) and is referred to as the "pin method." This procedure involves the use of Merrifield solid phase peptide synthesis, in which one end of a growing polypeptide chain is covalently linked to an insoluble support. In this case, a comb-like arrangement of dozens of pins are dipped into differentially filled aliquots of amino acids, thereby providing a defined discrete set of synthetic peptides, with a unique sequence at the head of each pin. Thus a large group of linear peptides could be rapidly synthesized and, if necessary, deprotected and assayed while still attached to the solid support. Alternatively, the peptides could be cleaved from the support and independently characterized and tested.

The second major development in multiple synthesis involved work by Houghten, R. A., *Proc. Natl. Acad. Sci. U.S.A.*, 82, 5131–5135 (1985). In this procedure, different peptides are simultaneously prepared by solid phase methods, but individual peptide sequences are segregated from one another, when required, by being held in solvent-permeable plastic bags (the "tea-bag" method). Selected packets are removed and subjected to their own chemistries (adding different amino acids at one position) and then recombined when common amino acids are used to minimize the synthetic workload. Thus, a series of 10 linear peptides of sequence A-B-$X_n$-D-E can be prepared with $X_1$–$X_{10}$ merely be separating the 10 packets after adding a common amino acid, "D", then recombining the packets after adding $X_n$ to carry out couplings of B and A.

Further studies have been conducted by Houghten, Fodor and Hruby which describe the preparation of linear peptide libraries using modified peptide synthesis methods, while the synthesis group used genetic engineering techniques to prepare the peptide mixtures. The common theme of all these approaches is that literally millions of synthetic linear peptides can be prepared, more or less simultaneously, and that these peptide libraries can then be screened, collectively or in smaller groups, against specific antibodies or in bioassays for discovery of new lead compounds for various clinical problems. In this way, diversity of structures, meeting or exceeding the diversity found in natural products from rain forests or ocean dwellers, can potentially provide a rich new source of compounds for analysis by the pharmaceutical industry.

All of the above methods produce linear peptides. Most techniques use the most common twenty amino acids in their examples; however, this is not an inherent limitation. The use of unnatrual amino acids (optically active isomers) provides a new challenge in terms of product characterization. Most analytical methods for peptide structural characterization, including amino acid analysis and peptide sequencing, are most useful when applied to compounds containing only the twenty natural amino acids.

However, Kerr et al. (*J. Amer. Chem Soc.*, 115, 2529–2531 (1993)), used a dimeric sequence formed using the trifunctional amino acid lysine with two difference sequences on each of the dimeric arms. One is composed of a least some unusual amino acids while the second arm contains a "coded" sequence composed only of common amino acids that may be readily sequenced. If the pairs of sequences in a peptide library are carefully coordinated, this approach combines the greater diversity available by using unnatural amino acids, but also contains a resident and covelantly lined reading code that can be used for sequencing. Obtaining the sequence of the unique natural amino acid arm automatically reveals the sequence of its paired arm since the molecules are prepared concomitantly.

The use of peptide libraries generates structurally diverse compounds, wherein, each of those linear hexapeptides contains at least two backbone rotatable bonds which, in linear form, are quite free to rotate. In a hexapeptide, if only 60° angle increments are considered, one must incorporate another $6^6$ or 46,000 other variables for each peptide, since linear peptides are inherently flexible. This suggests that one is likely to see both many false positives and false negatives since conformational as well as structural diversity now plays such a major role.

While some recent versions of peptide combinational libraries may approach the theoretical maximum (Avogadro's number) of different structures in a molar unit of library product, the flexibility which is common to linear products is a significant limitation compared to the variety of conformational constraints that are found in most potent pharmaceuticals.

In order to synthesize a single defined peptide sequence those skilled in the art generally use the Merrifield method to "grow" peptide chains attached to solid supports. The process of synthesizing these individual peptides has been automated. Commercially available equipment can be used to synthesize peptides of one hundred or more amino acids in length. To obtain peptides of arbitrary length, the resulting peptides can be ligated with each other by using appropriate protective groups on the side chains and by employing techniques permitting the removal of the synthesized peptides from the solid supports without deprotecting them. Thus, the synthesis of individual peptides of arbitrary length is known in the art.

Combinatorial peptide libraries described to date have involved linear sequences. This is the case whether chemical (primarily solid phase peptide synthesis) or biological (combinatorial DNA libraries) techniques have been used for preparing the linear compunds.

Linear peptides are generally flexible molecules with entropic limitations on achieving productive biologically active conformers. For this reason many authors have described the advantages of using various types of conformational and topographical constraints to reduce these degrees of freedom (for example, see F. J. Hruby, $Life\ Sci.$, 31, 189 (1982) and V. J. Hruby et al., $Biochemical\ J.$, 268, 249, (1990)). These constraints may involve amide bond replacements, backbone and side chain alkyl substituents (to fix $\phi$, $\psi$, and $\chi$-space), and use of heterocyclic amino acids such as proline (Pro) or tetrahydroisoquinoline carboxylic acid (Tic), among many other possibilities.

All of the above techniques focus on linear peptide mixtures; however, a preferred method of constraining peptides involves cyclization. Cyclic peptides may be prepared in which the ring is formed by oxidation of the naturally occurring cysteine residues yielding a disulfide bridged structure. This technique mimics the most common form of cyclization found among naturally occurring peptides and proteins but does not provide a convenient means of preparing other types of cyclic structures.

In order to prepare cyclic peptides, the most common technique used to employ amino acids with orthogonally protected functional groups such that some are removable selectively in the presence of others. Those skilled in the art can use these techniques to prepare peptides in solution in which the amino terminus is cyclized to the carboxyl terminus to form a ring. A naturally occurring example is the antibiotic gramicidin. Alternatively pairs of cysteine residues are oxidized to disulfide bonds to form one or more rings; the familiar naturally-occurring cyclic peptide hormone ocytocin is an example of such a structure, such as has been prepared by O'Neil et al., $Protein$, 14, 509–515 (1992)); however, this example is limited to cases of disulfide forming cyclic hexapeptides.

An alternate approach to solving the problem of structural diversity is to utilize other means of forming cyclic peptides include side chain-to-side amide bonds or side chain-to-backbone linkages. By combining the use of Merrifield (or related) solid phase methods with various solution cyclization procedures, it has proven possible to prepare many examples of known peptide hormones or their analogs.

If cyclization is of the head-to-tail variety, several advantages accrue. First the molecule is far more likely to have a reduced number of conformational states available to it. This can often lead to more potent and/or more selective ligands to biological receptors or to tighter binding to antibody molecules. Examples in the literature include a $\delta$-selective opioid analog known as DPDPE, a mini-somatostatin cyclic hexapeptide (Merck), and a potent and selective endothelin antagonist, BQ-123 (Banyu).

A second advantage of head to tail cyclic peptides is that the molecule is virtually resistant to two of the three major types of proteolytic enzymes. Neither aminopeptidases nor carboxypeptidases are activated since cyclization simultaneously removes both amino ($NH_3+$) and carboxylate ($COO-$) termini. The molecule's resistance to endopeptidases is also likely to be affected but not in any predictable fashion.

Because of the above factors, any lead compounds obtained in a drug screening assay of cyclic peptide libraries are far more likely to resemble the final target peptide-inspired pharmaceuticals. This is especially true if D-amino acids and other unusual amino acids are incorporated into the library pool, giving rise to an even greater diversity of potential target analogs.

Finally, small cyclic compounds (with 4, 5, 6 amino acid residues) are more likely to possess decreased conformational flexibility than libraries of greater ring size. Nevertheless, the greater structural diversity inherent in the larger rings could provide more examples of lead structures and are included in the disclosure, even though the preferred embodiment involves compounds containing 408 residues in the ring, with 5 and 6 residue rings being preferred in view of their greater ease in forming cyclic structures (see Table II below).

TABLE II

Calculated Combinations of Cyclic Peptides (Head-to-Tail) Cyclizations); Based on Asp-Resin

| No. of residues in ring | Linkage to resin | With 19 amino acids at variant positions | With 38 amino acids at variant positions |
| --- | --- | --- | --- |
| 4(cyclic tetrapeptides) | Asp | | |
| | Asp;Gln | 6,859 | 109,744 |
| | Asn;Gln | 27,436 | 438,976 |
| 5(cyclic pentapeptide) | Asp | | |
| | Asp;Gln | 130,321 | 2,085,136 |
| | Asn;Gln | 521,284 | 8,340,544 |
| 6(cyclic hexapeptide) | Asp | | |
| | Asp;Gln | 2,476,099 | 3,010,936,300 |
| | Asn;Gln | 9,904,396 | 12,043,745,000 |

Although the synthesis of a particular peptide may be routine, it is necessarily laborious. This presents a large practical problem in a situation where it is not previously known which of a mulitiplicity of peptides is, in fact, the preparation desired. While it is theoretically possible to synthesize all possible candidates and test them with whatever assay is relevant (immunoreactivity with specific antibody, interaction with a specific receptor, particular biological activity, etc.), to do so using the foregoing method would be impractical. In general, the search for suitable peptides for a particular purpose has been conducted on in cases where there is some prior knowledge of the most probable successful sequence. Therefore, methods to systematize the synthesis of a multiplicity of peptides for testing in assay systems would have great benefits in efficiency and economy, and permit extrapolation to cases where nothing is known about the desired sequence.

Three such methods have so far been disclosed. One of them, that of Houghten, R. A., Proc. Natl. Acad. Sci. U.S.A., 82, 5131–5135 (1985), is a modification of the above Merrifield method using individual polyethylene bags. In the general Merrifield methods, the C-terminal amino acid of the desired peptides is attached to a solid support and the peptide chain is formed by sequentially adding amino acid residues, thus extending the chain to the N-terminus. The additions are carried out in sequential steps involving deprotection, attachment of the next amino acid residue in protected form, deprotection of the peptide, attachment of the next protected residue, and so forth.

In the Houghten methods, individual polyethylene bags containing C-terminal amino acids bound to solid support can be mixed and matched through the sequential attachment procedures so that, for example, twenty bags containing different C-terminal residues attached to the support can be simultaniously deprotected and treated with the same protected amino acid residue to be next attached, and then recovered and treated uniformly or differently, as desired. The result of this is a series of polyethylene bags each containing a different peptide sequence. Although each bag will contain many peptides, all of the peptides in any one bag are the same. The peptides in each bag can then be recovered and individually biologically tested.

An alternative method has been devised by Geysen, H. M., et al., *Proc. Natl. Acad. Sci. U.S.A.*, 81, 3998–4002 (1984). See also WO86/06487 and WO86/00991. This method is a modification of the Merrifield system wherein the C-terminal amino acid residues are bound to solid supports in the form of polyethylene pins and the pins treated individually or collectively in sequence to attach the remaining amino acid residues. Without removing the peptides from support, these peptides can then efficiently be effectively individually assessed for the desired activity, in the case of the Geysen work, interact with a given antibody. The Geysen procedure results in considerable gains in efficiency of both the synthesis and testing procedures, while nevertheless producing individual different peptides. It is workable, however, only in instances where the assay can be practically conducted on the pin-type supports used. If solution assay methods are required, the Geysen approach would be impractical.

A third method described by Huebner and Santi, U.S. Pat. No. 5,182,366, describes a procedure in which linear peptide mixtures may be prepared using mixed resins such that any particular resin has attached to it a single unique sequence. This is achieved by a series of splitting and recombining of resin pools such that only one amino acid is coupled at a single time in each pool, but following that completed reaction, the pools are recombined such that a large number of the statistically calculable representations are prepared by extending this through n steps.

In principle the methods of preparing linear peptide libraries might be extended to the preparation of cyclic peptide mixtures (see Table III below).

TABLE III

Proteced Amino Acids Used in Example 3; Total of 1296 Peptides

INITIAL ATTACHMENT:

Boc-Asp-OFm (bound to resin)

| Cycle 1 | Cycle 2 | Cycle 3 | Cycle 4 |
|---|---|---|---|
| Boc-Gly | Boc-Arg | Boc-Lys (GlZ) | Fmoc-Ala |
| Boc-Tyr (Cl, Bzl) | Boc-Gly | Boc-Ala | Fmoc-Phe |
| Boc-Val | Boc-Trp (For) | Boc-Thr (Bzl) | Fmoc-Tyr (OBut) |
| Boc-Leu | Boc-Phe | Boc-Phe | Fmoc-Ile |
| Boc-Ser (Bzl) | Boc-Met | Boc-Pro | Fmoc-His (Fmoc) |
| Boc-Glue (OCHx) | Boc-Gln | Boc-Glue (OChx) | Fmoc-Gly |

But most peptide cyclizations are carried out in solutions under high dilution conditions in order to avoid dimerization and polymerization. Furthermore, attempting to cyclize mixtures of linear sequences would predictably lead to virtually intractable products with numerous unidentifiable and inseparable components.

Most peptide libraries involve the use of Merrifield solid phase synthesis to insure synthetic ease and feasibility. This approach is normally not compatible with end to end cyclization, since the C-terminal residue is usually the point of attachment, thereby precluding cyclization without first cleaving the peptide. Cleaving the peptide from the solid support creates two new problems: 1) making possible dimeric and oligomeric linear and cyclic structures, and 2) rendering the process of characterizing and retaining groups of identical peptides nearly impossible.

It is known that peptide libraries can provide a novel pool of target compounds. It is also known that there are many advantages to cyclic peptides, but most known methods of preparing peptide libraries are not amenable to the preparation of cyclic peptides. In a paper describing linear peptides (Lam et al., *Nature*, 354, No. 7 (1991), the authors mention the possibility of cyclic peptides, but that reference does not teach the preparation of these. In a paper by O'Neil et al., *Proteins*, 14, 509–515 (1992), cyclic peptide mixtures are constructed on the surfaces of phages but the compounds are not proven to be cyclic and the ring is formed by disulfide oxidation of cysteine.

Using peptide synthesis techniques, the present invention describes an innovative method for preparing libraries of cyclic peptides using resin-bound cyclization that is compatible with the presence of other peptides on accompanying beads and even on the same bead. The present invention further demonstrates the feasibility of this technique by synthesizing, both individually and collectively, cyclic peptides and by fully characterizing the products to demonstrate their structural and stereochemical integrity. This invention also solves the problem of dimerization and it is demonstrated that the resin-bound cyclization produces an monomeric cyclic components.

SUMMARY

This invention involves a method for preparing mixtures of cyclic peptides using novel solid phase methods. One of the amino acid constituents, either a bifinctional or trifunctional amino acid, is attached to the solid support using either a side chain functional group or through its amine group forming in the latter case a secondary amine with the characteristics of proline, a well-known cyclization inducing amino acid. The chain is elongated with appropriate side chain, amine, and carboxylic acid protecting groups. The N- and C-terminal protecting groups are removed. Cyclization is performed on the solid support, yielding a mixture of products, some with remaining side-chain protected functionality. The mixture is subjected to one of several possible cleavage methods and can be simultaneously released from the solid matrix if desired. The result is a soluble mixture of cyclic peptides that can be used for a variety of biological tests to screen for a desired function.

Abbreviations follow the recommendations of the IUPAC-IUB Commission on Biochemical Nomenclature (*Biochem. J.*, 126, 773–780 (1972)). Abbreviations, symbols, and terminology as utilized herein set forth in Table IV attached hereto.

TABLE IV

A listing of the abbreviations, symbols, and terminology as utilized herin

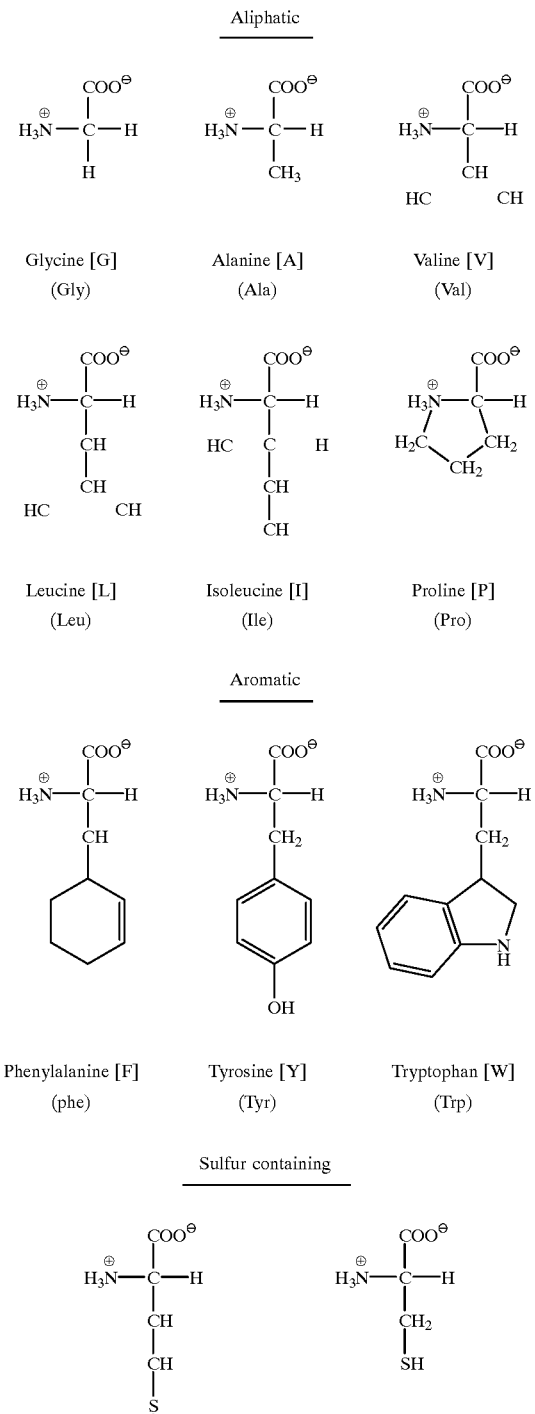

TABLE IV-continued

A listing of the abbreviations, symbols, and terminology as utilized herin

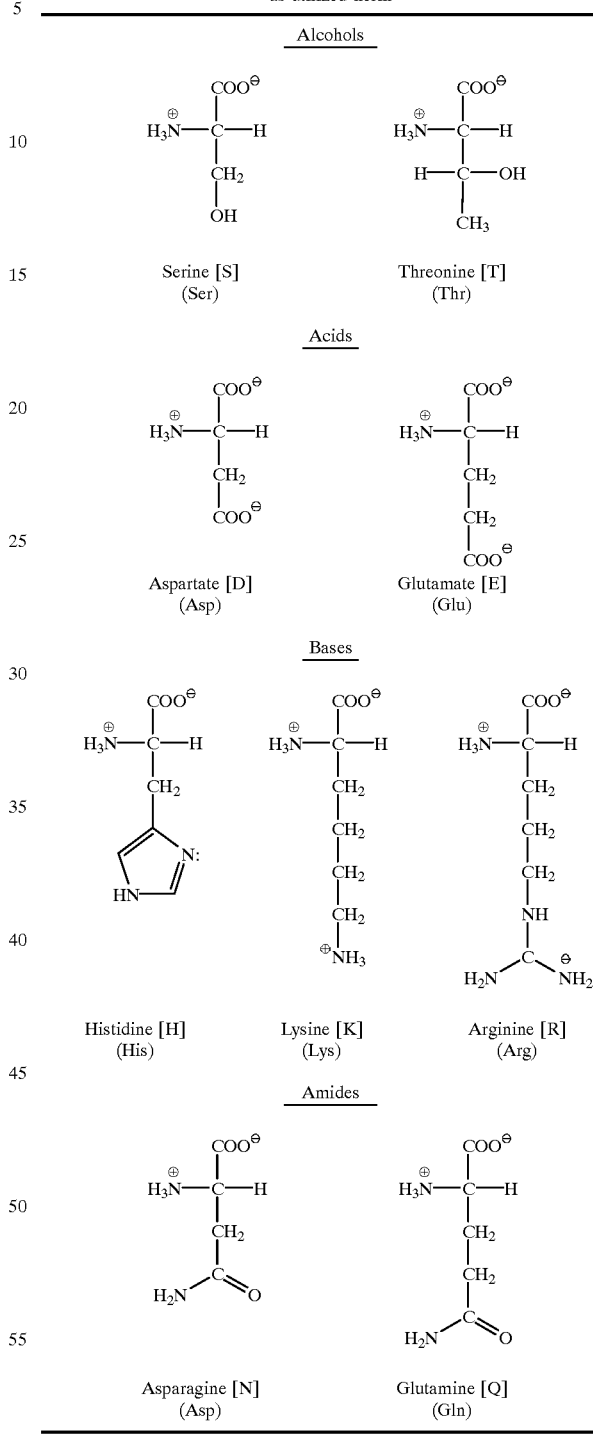

There are many ways to prepare cyclic peptides. In most higher organisms cyclic peptides are usually found in the form of disulfide-bridged structures as a result of the oxidation of cysteine residues to cysteine. In the laboratory and in lower organisms, a great many other forms of cyclic peptides are found including side chain to side chain and backbone-to-side chain structures. In this invention we describe the preparation of head-to-tail cyclic peptides by way of a lactam (amide) bridge.

In principal, the number of possible cyclic peptides assuming use of 20 common amino acids and a ring consisting of n residues is $20^n$ (Table I). For example, there would be nearly 3,200,000 possible cyclic pentapeptides (this number is reduced somewhat due to symmetry in some sequences). If one of the positions is fixed due to attachment to a solid support, the total possible structures is reduced. Thus as shown in Table V, there are now only 160,000 possible cyclic pentapeptides with one position fixed as aspartic acid, 160,000 examples with a fixed lysine, 160,000 examples with a fixed asparagine and so on.

TABLE V

Number of possible cyclic peptides with a single fixed position

| RING SIZE # OF RESIDUES | FIXED AMINO ACID AT POSITION 1 (ASP or LYS, ETC.) | $20^n$ n = VARIABLE POSITIONS | TOTAL NUMBER OF PEPTIDES |
|---|---|---|---|
| 4 | 1 | $20^3$ | 8,000 |
| 5 | 1 | $20^4$ | 160,000 |
| 6 | 1 | $20^5$ | 3,200,000 |
| 7 | 1 | $20^6$ | 64,000,000 |
| 8 | 1 | $20^7$ | 1,280,000,000 |

A preferred embodiment of this invention involves the incorporation of an additional turn inducing amino acid or imino acid analog within the linear precursor of the solid-support-linked cyclic peptide. Such turn inducers include proline, other imino acids including N-methyl amino acid, glycine, or flexible pseudodipeptides such as $\text{Pro}\psi[\text{CH}_2-\text{S}]\text{Gly}$. These replacements would be expected to improve the quality of the cyclic products while in most cases reducing the number of conformationally accessible structures. In contrast to linear peptide mixtures, cyclic peptides and cyclic pseudopeptides reduce enzyme degradation by exopeptidases and reduce mobility, thereby enhancing the prospects for productive interactions with receptors, antibodies, metal ions or other molecular recognition targets.

The incorporation of a fixed turn-inducer at one position reduces the number of potential cyclic peptides in a given mixture. Table VI contains a representative array of cyclic peptides assuming a ring size of n amino acids wherein one position is fixed and attached to the solid support and a second position is fixed and consists of a turn-inducing residue.

TABLE VI

The theoretical number of cyclic peptides when both support-linked amino acid and a turn-inducing amino acid are incorporated within cyclic peptides of varying ring size

| Ring Size | Example of Support-Linked Amino Acid | Example of Turn-Inducer at N-1 Positions | Remaining Variable Positions ($20^{n-2}$) | Total # of Peptides in Mixture |
|---|---|---|---|---|
| 5 | Asp | Pro(4) | $20^3$ | 4 × 8,000 |
|   | Lys | Pro(4) | $20^3$ | 4 × 8,000 |
|   | N-linked AA | Pro(4) | $20^3$ | 4 × 8,000 |
| 6 | Asp | Pro(5) | $20^4$ | 5 × 160,000 |
|   | Lys | Pro(5) | $20^4$ | 5 × 160,000 |
|   | N-linked AA | Pro(5) | $20^4$ | 5 × 160,000 |
| 7 | Asp | Pro(6) | $20^5$ | 6 × 3,200,000 |
|   | Lys | Pro(6) | $20^5$ | 6 × 3,200,000 |
|   | N-linked AA | Pro(6) | $20^5$ | 6 × 3,200,000 |

Assuming that there are 20 amino acids in each of the n−2 remaining variable positions, the table contains the total number of possible cyclic peptides in each sublibrary. By varying the position of the turn-inducing residue, a set of n−1 sublibraries is effectively created. In a preferred embodiment, these sublibraries are separately tested for the desired biological or other activity in order to deconvolute the cyclic library mixture and establish the fraction(s) to be chosen for further analysis and deconvolution. If each one of the variable (n−2) positions is serially held constant, and again assuming 20 amino acids per position then n−2 (20) new sublibraries are created. When these are individually tested, then a consensus subset of possible peptides will result that will suggest a smaller group of individual peptides that may be synthesized to combine the optimized residue(s) at each position.

Conventional peptide cyclization employs side chain to side chain or N-terminal to side chain condensation as well as a disulfide bridge formation. The present peptide cyclization process utilizes solid-phase synthesis of cyclic peptides containing an Asp residue in their sequence in the preferred embodiment; however, other residues amenable to side chain or backbone attachment as described hereafter may also be used. To illustrate the concept, a synthesis on a cyclic peptide mixture is described in which the resin-bound amino acid is a side-chain linked aspartic acid (Asp) residue.

Synthesis is performed starting from the Asp residue linked to a Merrifield to PAM resin through the β-carboxylic function and protected by a fluorenylmethyl ester on the α-carboxylic group. Additional amino acids are added either as a weighted mixture or as individual entities using a split resin strategy as applied to linear peptides. Once the linear precursors have been synthesized by the Boc/benzyl method and the Boc protecting group on the N-terminal amino function(s) have been removed with TFA, the C-terminal carboxyl group of the Asp residue is selectively deprotected with piperidine and cyclization of the peptide mixture's accomplished by the BOP method, or other cyclization procedure using improved cyclization methods. A preferred embodiment of the present invention involves use of the recently described reagent, HATU, whose advantages are best revealed in Example 3 hereafter. Final HF deprotection of the side chains of trifunctional residues, with concomitant cleavage from the resin gives the cyclic peptide mixture as a well-defined mixture of good purity in reasonable yield.

Furthermore, the present invention solves the problem of conformational constraints by providing a method for preparing libraries of cyclic peptides. The procedure described and claimed herein relies on various perturbations of solid phase methods and the diverse protection/deprotection methods currently available. Resin bound cyclization is utilized in order to avoid dimer/oligomeric complications and to provide the one-bead/one-(cyclic) peptide optimalization technique.

The present invention offers an alternative to all previously described versions of linear peptide libraries in that it provides an efficient and practical method of preparing mixtures of cyclic peptide libraries. The specific procedures have been shown to provide clean mixtures of cyclic peptides. For example, initial problems involving formation of truncated linear sequences have been virtually eliminated by employing additional washes to eliminate residual amine-containing impurities. Problems of racemization or epimerization have also been solved by improved synthetic procedures. These were found through an exhaustive examination of all individual steps to identify and optimize each of the stereochemistry-altering steps.

Also, new improved coupling agents have been employed to drive the cyclization reactions to completion in a short period of time. By minimizing the exposure of the sequences to cyclization conditions, less epimerization occurs at the C-terminal residue, and more sensitive amino acids such as tryptophan or histidine are less subject to byproduct formation.

This disclosure presents for the first time a viable synthetic approach that is compatible with the formation of cyclic peptide libraries of known amino acid composition. Significant advantages are realized by the use of cyclic peptides prepared by the procedures of the present invention in terms of reducing the inherent flexibility of linear sequences and in stabilizing the peptides against many forms of proteolytic degradation. The demonstration that mixtures of cyclic peptides can be efficienctly and reliable made using a modified technique of resin-bound cyclization thus opens the door to an improved era of screening for cyclic peptide lead structures and more rapidly obtaining assay results using millions of cyclic candidate structures with a combination of structural diversity and conformational constraints.

Moreover, the present invention solves the problem of preparing cyclic peptide libraries by invoking the concept of resin bound cyclization as shown in FIG. 1. This approach achieves an end-to-end cyclization by linking the amino acid to a solid support via its side chain. A limitation to this procedure is the requirement of a trifunctional amino acid, most usually lysine or ornithine, aspartic acid or glutamic acid, somewhere in the sequence of the peptide. But by using the amine attachment strategy (described in detail below) this limitation is effectively overcome.

Using earlier examples of cyclic hexapeptides and limiting only one of the six positions to four (rather than twenty or so) common amino acids will result in a reduction of only about a factor of five to the millions of peptides accessible by this technique. Using D-amino acids, the same factor of five is used theoretically to reduce the total number of possible peptides from over 3 billion to 500 million. Similarly, using cyclic heptapeptides, this approach will nevertheless provide a fairly diverse group of over 17 billion compounds. (See Table II). If a cyclization-inducing amino acid (proline, N-Alkyl amino acids, pseudopeptides) is incorporated, the resulting number of analogs is still quite large (Table VI).

In order to expand the range of cyclic peptide mixtures, a new strategy for the solid phase synthesis of head-to-tail lactam cyclic peptides is described. In this new strategy, instead of attaching the first C-terminal amino acid via its side chain to the resin, the C-terminal amino acid can be attached to the resin via its amine functionality (FIG. 2). This procedure allows for the efficient preparation of cyclic peptide mixtures (libraries) analogous to the approach previously reported by our group (J. J. Wen and A. F. Spatola, "Synthesis and Characterization of Pseudopeptide Libraries," 207th ACS national meeting, March, 1994, San Diego, Calif.).

As shown in FIG. 2, the carboxyl group of the C-terminal amino acid will first be protected by the formation of its allyl or trimethylethyl ester, followed by reaction with a benzylaldehyde resin derivative. The resin derivative in turn can be prepared by several steps starting from commercially available 2-hydroxy-4-methoxybenzaldehyde (FIG. 3).

Further peptide elongation is carried out by following standard Fmoc-based peptide synthesis procedures (E. Atherton and R. C. Sheppard, *Solid Phase Peptide Synthesis, IRL Press, Oxford,* 1989; G. B. Fields and R. L. Noble Int. J. *Peptide Protein Res,* 35, 161–214, (1990)). Finally, the N- and C-terminal protecting groups can be deprotected separately, and the desired cyclic peptide is obtained by carrying out the cyclization reaction directly on the resin with uronium-based coupling reagents, followed by mild TFA cleavage of peptide from the resin. This strategy provides a distinct advantage over previous strategies mentioned above, since the C-terminal amino acid can be any common amino acid (excepting proline), and not necessarily a trifunctional amino acid.

Thus, present invention teaches the novel approach of expanding peptide libraries to provide libraries of cyclic peptides. Many of the innovations developed in previous inventions, such as the "one bead-one peptide" concept of Lam, K., Salmon, S., Hersh, E, Hruby, V., Kazmierski, W., and Knapp, R., (*Nature, Vol.* 354, Nov. 7, 1991), incorporated herein are applicable to the preferred embodiment. Moreover, the laser-based deprotection of NVOC-protected amino acids embodied in the U.S. Pat. No. 5, 143,854, Pirrung et al., and incorporated herein, may be applied hereto. The present invention provides for cyclic peptide libraries simplifying the problem of identifying the specific sequences and localizing them during the process of a bioassay.

The advantages of cyclic peptides for providing useful therapeutic agents in and of themselves can be readily assessed by recent advances in such diverse areas as endothelin antagonists and RGD-containing sequences. A very promising cyclic pentapeptide that has potent and selective endothelin antagonism was found during routine screening of microbial mixtures. More reasonably potent and constrained analogs of RGD peptides have been prepared involving various peptide cyclization strategies.

Cyclization is an effective method for significantly reducing the larger number of degrees of freedom inherent in linear compounds with multiple rotatable bonds. For peptides this solution is most practical for rings of 12–36 atoms (4–12 amino acid residues). In order to effect head-to-tail cyclizations, trifunctional amino acids or backbone-linked amino acids are linked to the solid support via the side chains or there amine groups in the initial attachment step. Using side chain attachment, the preferred group includes Asp, Glu, Lys, Orn, Asn, and Gln. Other positions may be occupied by any of the common or unnatural amino acids, thus providing significant structural diversity, especially if D-amino acids are included. For example, a typical cyclic hexapeptide with Asp linkage yields up to $1 \times 39 \times 39 \times 39 \times 39 \times 39$, or over $3.5 \times 10^9$ structures.

When using the amine group for attachment of the amino acid to the support, virtually all common acids (excepting proline or other imino acids) can be attached to the solid support in the initial position. The peptide chain can be lengthened by adding mixtures of various amino acids until the desired length is reached. Alternatively a given position may be lengthened by adding only a single amino acid to provide a self-deconvoluting set of sublibraries. A further advantage of using the amine group for attachment of the peptide chain is that this aids in the cyclization of the linear peptide mixtures thus produced through the well-known "pseudo-proline" effect. Additionally, the incorporation of an amino acid within the sequence reduces hydrogen bonding and the aggregation problem that has been cited as a problem leading to dimerization of peptides during the cyclization step. Thus a further advantage of the instant invention accrues in that both side chain and the amine attachment approach lead to minimization or elimination of the dimerization problem.

The synthetic scheme of the present invention describes a synthetic protocol that was utilized to prepare mixtures of cyclic pentapeptides, cyclic hexapeptides, and cyclic heptapeptides. (See Example 1) (FIG. 4). Box-Asp-OFm was linked to the resin and Boc chemistry was used to elongate the chain. Final N-termination deprotection with acid and treatment with 20 percent piperidine to cleave the C-terminal OFm ester was followed by resin-bound cyclization with BOP-HOPt. Various peptides were prepared both individually and in small groups. Results were comparable although the cyclization did result in varying amounts of epimerization of the C-terminal aspartyl residue. This was confirmed by the preparation of a corresponding sequence using Boc-D-Asp-OFm.

The peptides have been characterized by amino acid analysis, NMR spectroscopy, by electrospray mass spectroscopy (positive and negative modes), and by FABMS, both as mixtures and, in some cases, individually. Groups or mixtures containing as few as 4 and 16 peptides, were prepared to assist in the characterization and optimization of the cyclic mixture synthesis, and this led to improved synthetic procedures that have solved the problem of significant amounts of undesired impurities.

As an alternative method of identifying products, CE-EC (capillary zone electrophoresis with electrochemical detection) may be used (with R. P. Baldwin and J. Ye, unpublished results). Using this method the electroactive species containing, for example, Trp and Tyr, have been observed, and the analogs with transparent functionalities (e.g., Asp, Leu, Ala, Gly) have been eliminated.

This invention provides a technique for preparing cyclic peptides on various solid supports. The type of support used may include standard polystyrene beads, membranes, pellicular supports (such as polyethylene glycol linked to polystyrene supports) or the recently described photolithographic techniques (U.S. Pat. No. 5,143,854, Pirrung et al.) using NVOC (photolabile) amino acids. The amino acids may be attached to the support by means of the amino acid side chains, or through the backbone using amine functionality.

The peptides may be cleaved from solid supports using a variety of techniques including mild or strong acid, strong base, photolysis, phase transfer catalysis, or catalytic transfer hydrogenation. A further technique, ammonolysis, can be used to provide peptide amides, or these may be prepared by acid cleavage using solid supports such as the various benzhydrylamine resins. If the amino acid is linked through a caroxylic acid side chain, such as Asp or Glu, the amide forming cleavages will give rise to two new related amino acids, asparagine (Asn) and glutamine (Gln), respectively. If the peptide mixtures are attached to the solid supports through a cleavable secondary amine function, release of the peptides provides an unmodified group of cyclic peptide products.

The examples given below describe the synthesis of cyclic pentapeptide, hexapeptide, and heptapeptide mixtures using either a side chain bound aspartyl (Asp) residue or an asparagine-linked product. Following a resin-bound cyclization of the deprotected amino and carboxyl termini, cleavage with strong acid yields a mixture of cyclic peptides (libraries) with a fixed Asp or Asn residue at a single position. The process can be extended using other side-chain acids (e.g., Glu) to yield Glu or Gln-containing cyclic peptides.

By modifying the initial linkage using a basic amino acid (such as lysine (lys) or ornithine (Orn)), a similar strategy has been used to prepare a variety of cyclic peptides with at least one basic residue in the sequence (FIG. 5). Other variations include linking hydroxy containing amino acids such as serine (Ser) or threonine (Thr) via a cleavable either linkage or ring substituted derivatives of phenylalanine or tyrosine through corresponding amino, carboxyl, or hydroxyl derivatives.

Alternative versions for preparing peptide libraries involves 1) backbone to side chain or 2) side chain to side chain strategies. Alternative and more general approaches involve amide bond formation using pairs of residues such as (Asp and Lys) or (Glu and Lys). However, these are in general more restrictive since they now limit the range of amino acid possibilities in two or even three positions as compared to the head-to-tail cyclization of the present invention which limits the only initial linking amino acid position.

The synthesis of cyclic peptide libraries and specified chemical synthesis of cyclic peptide mixtures using side chain attachment are formed by the following method.

The present invention comprises a method of preparing a mixture of cyclic peptides of known composition and containing a cyclic peptide with a specified desired sequence portion. Moreover, a method is described for the sequential cleavage of a specified portion of each cyclic peptide by using one of a combination of orthogonal cleavage reagents. The procedure involves the following four steps. First a specific trifunctional amino acid is attached to a solid support via its amine group or side chain while the amino and carboxyl termini are protected with individually removable protecting groups. Next the peptide-resin mixture is divided into a number of pools with each pool containing an equal molar amount of the mixture. The next step involves coupling of a different single amino acid to the resin mixture in each of the pools. In a fourth step, the pool mixtures are then recombined to obtain a complex peptide mixture containing each peptide in a retrievable and analyzable amount. The steps can be repeated until the peptide is of the desired length, at which point the combined mixture is subjected to specific reaction conditions that liberate a single amino group and a single carboxyl group in each chain. The resin-bound compounds are then treated with an appropriate condensation reagent and the reaction drive to completion. The resulting cyclic peptides are then detached from the solid support and subjected to various analytical and biological assays to establish the fidelity of the synthetic transformations, and assess whether the collective mixture of cyclic peptides has one or more desired biological properties. If subsets of the pools are found to possess desired activities, the identity of the positively-responding agents may be established by an iterative technique of resynthesis and reassay of smaller groups.

Moreover, the method may be modified in that the deprotected but still resin-bound cyclic peptide is assayed while attached to the resin. By using a specific antibody or an appropriate calorimetric assay with the modified method, the positively reacting peptides can be more readily observed and subsequently identified. The method may be further modified by binding the individual cyclic peptides to a single resin particle using separate types of linkages such that the assay and sequence identification steps may be carried out separately.

An important outcome of the development of this invention was the demonstration that the dimer formation is minimal. FIG. 6 provides a demonstration of how mass spectrometry was useful in establishing the presence of artifactual dimers that are not true synthetic dimers. FIG. 6 represents an electrospray (negative mode) analysis of a small mixture of cyclic pentapeptides differing only in their inital C-terminal attachment (a mixture of Asp, Asn, Glue, Gln, and Lys). Only the acid components are clearly visible in the spectrum. In the dimer region, the major peak observed is formed from aggregation of two difference (Asp+Glu) cyclic pentapeptides that could not have been produced by synthesis from this and other supporting evidence we may conclude that the present invention has overcome the dimerization problem and affords cyclic peptide mixtures in a state of amenable for meaningful subsequent analysis and deconvolution.

BRIEF DESCRIPTION OF THE DRAWINGS

A better understanding of the present invention will be had upon reference to the following description in conjunction with the accompanying drawings, wherein:

FIG. 1 shows a general schematic of the cyclic peptides synthesis of the present invention, using side chain attachments.

Figure 2:
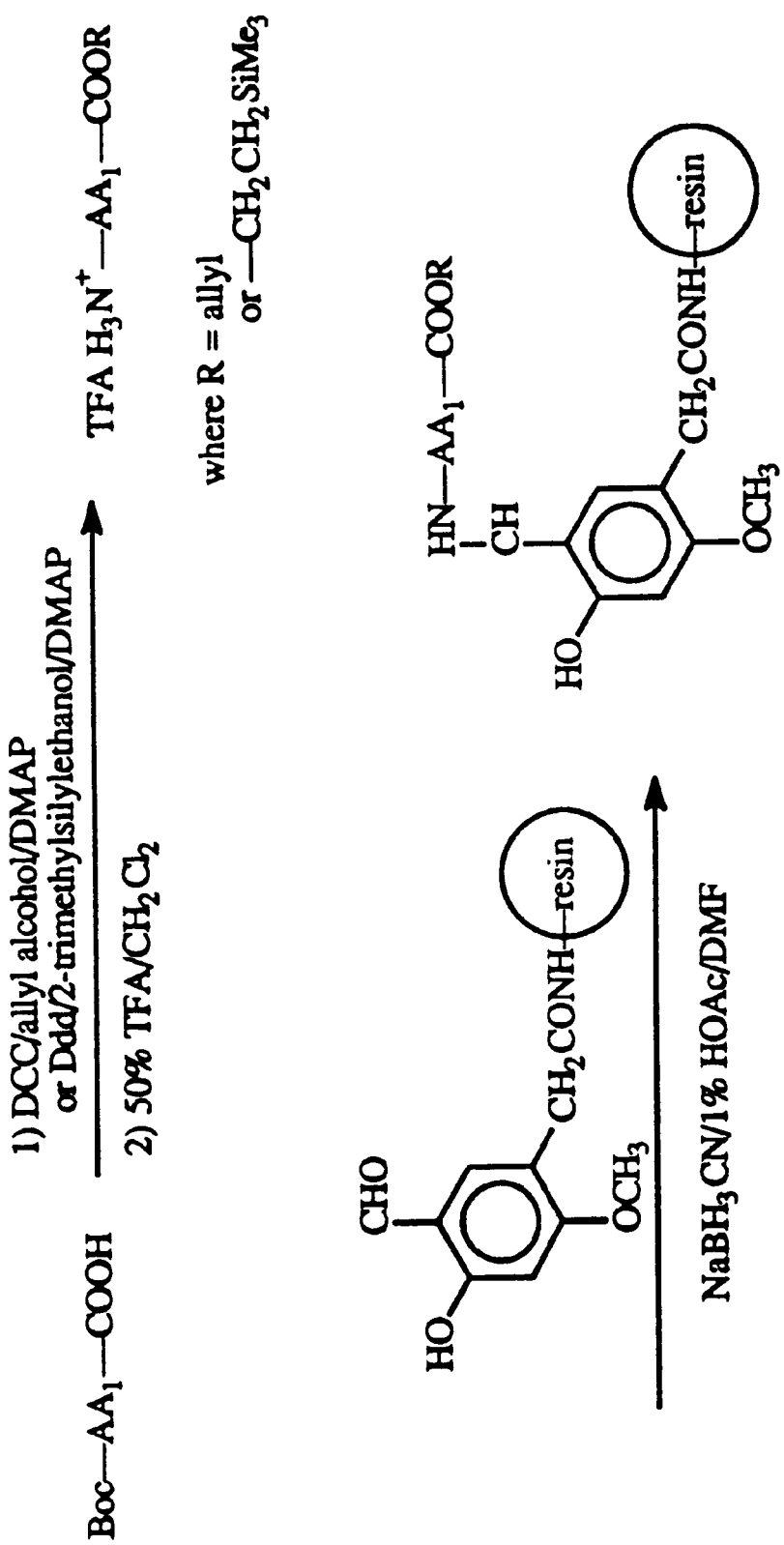
FIG. 2 shows a method for attachment of the first amino acid to a solid support using the backbone (primary amine unit) via an acid cleavable linkage.
Figure 3:
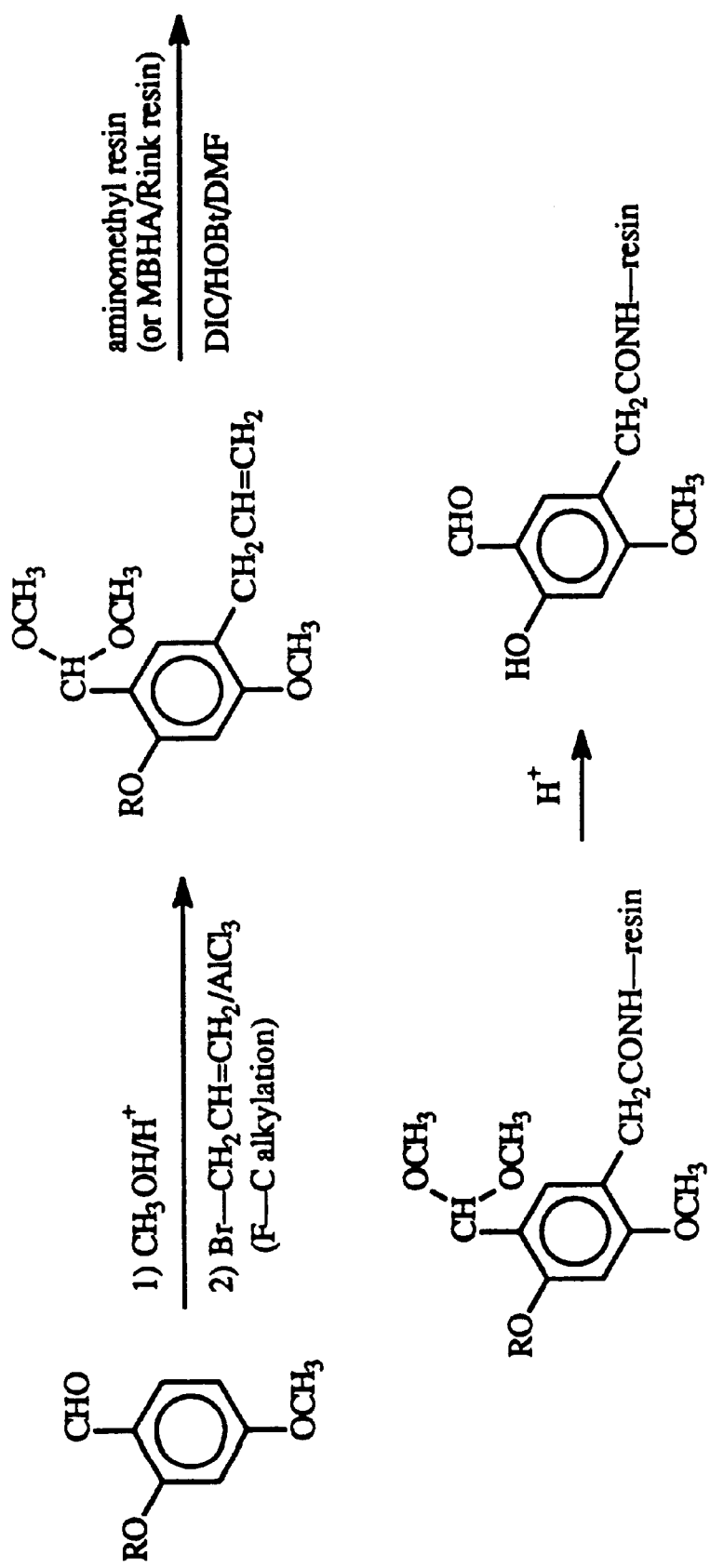
FIG. 3 describes the synthesis of a suitable linkage for attachment of a carboxy protected amino acid to the solid support using the amine group.
Figure 4:
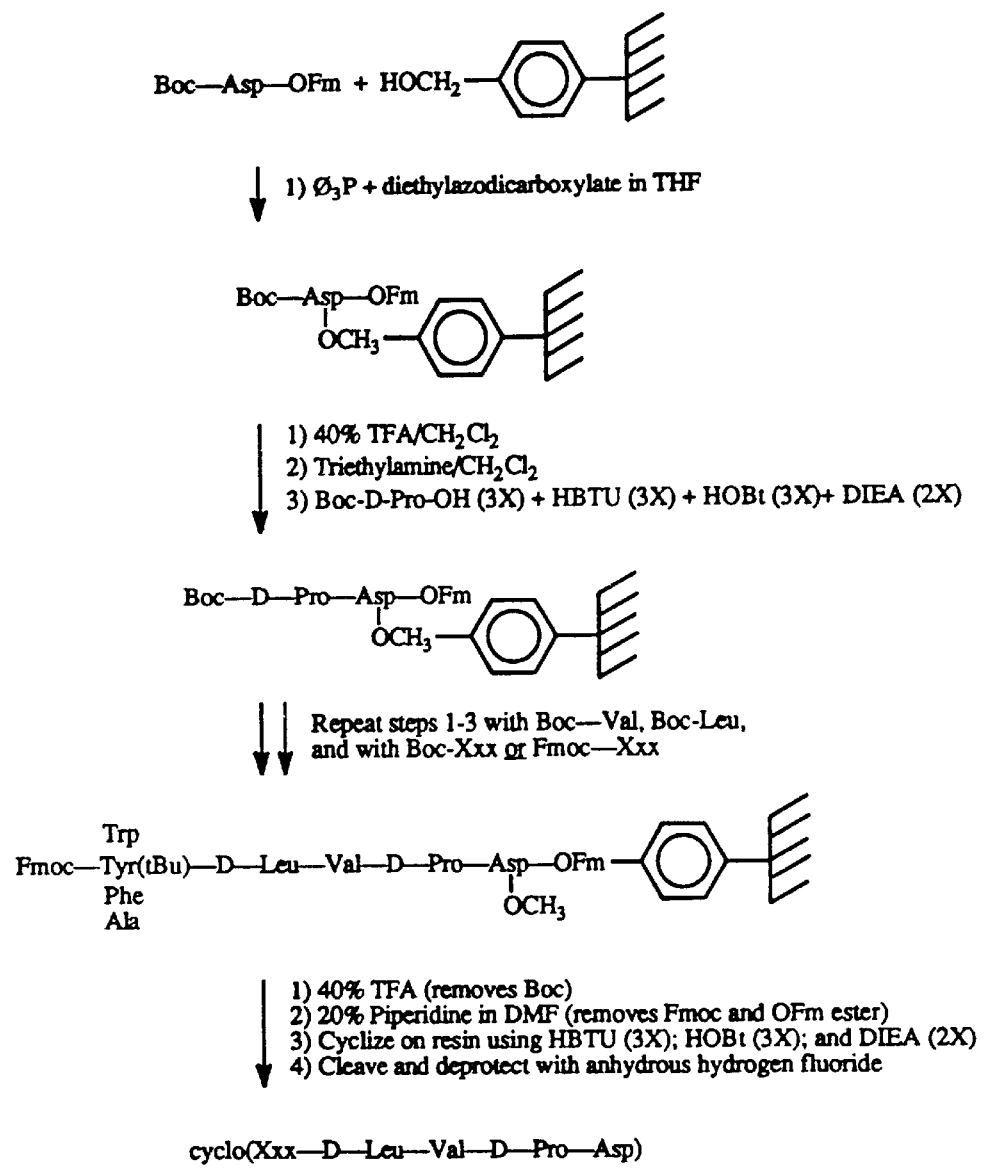
FIG. 4 shows a specific example of the preparation of a cyclic peptide in accordance with the schematic of FIG. 1.
Figure 5:
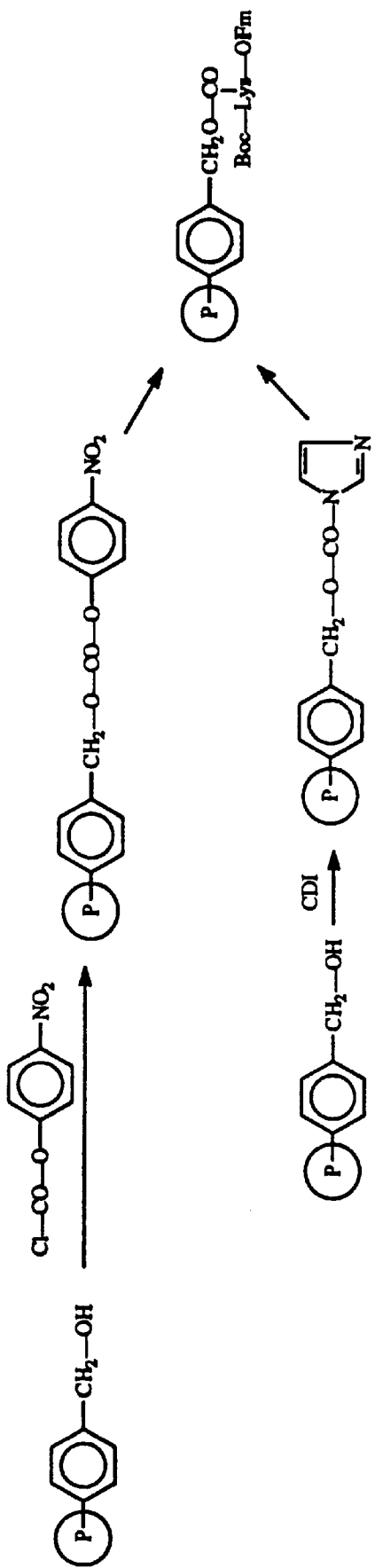
FIG. 5 shows the chemistry used to attach Boc-Lys-OFm to a hydroxymethyl resin.
Figure 6:
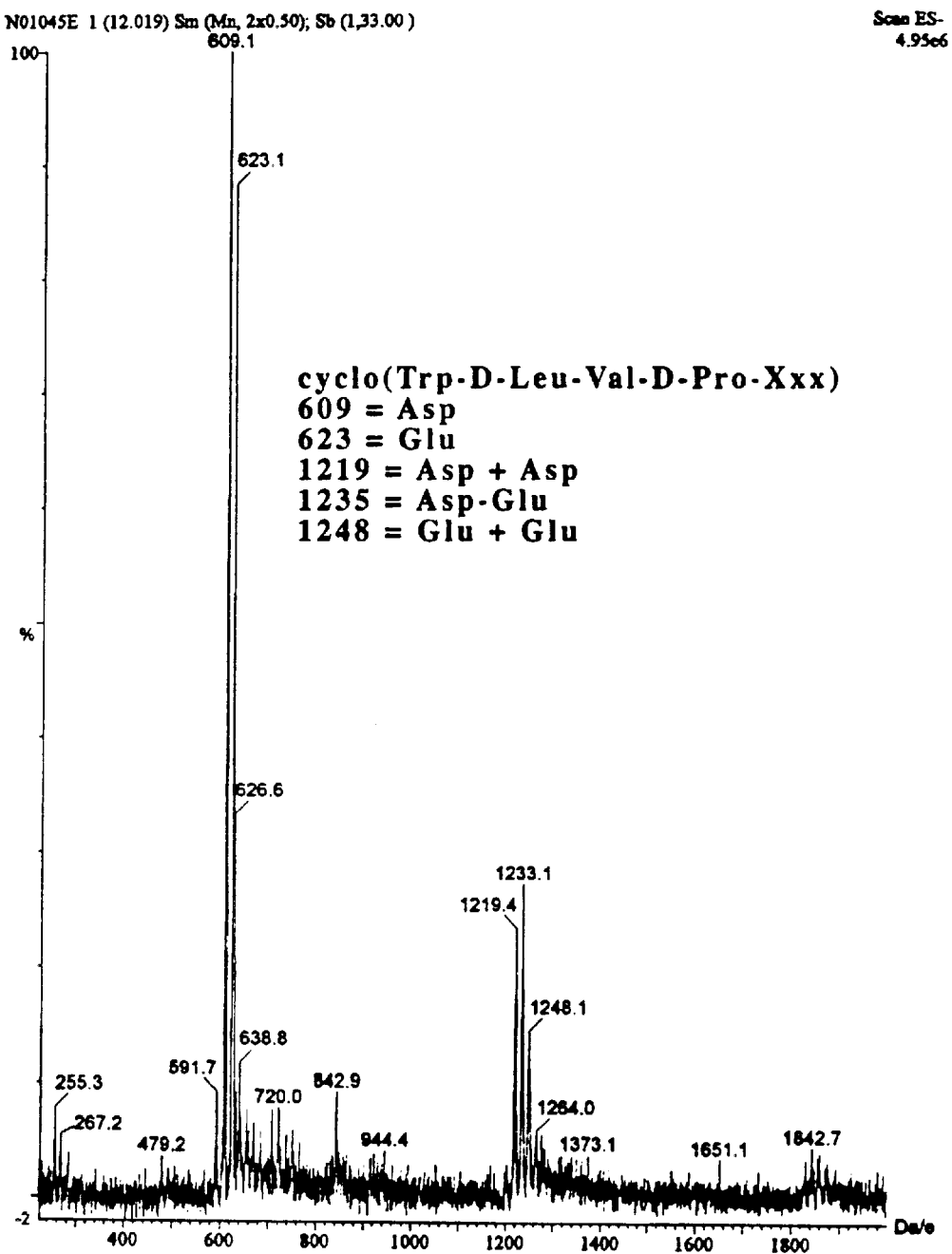
FIG. 6 shows an electrospray spectrum of a mixture of cyclic pentapeptides which demonstrates both the selectivity of the method and the aggregation of peptides.
Figure 7:
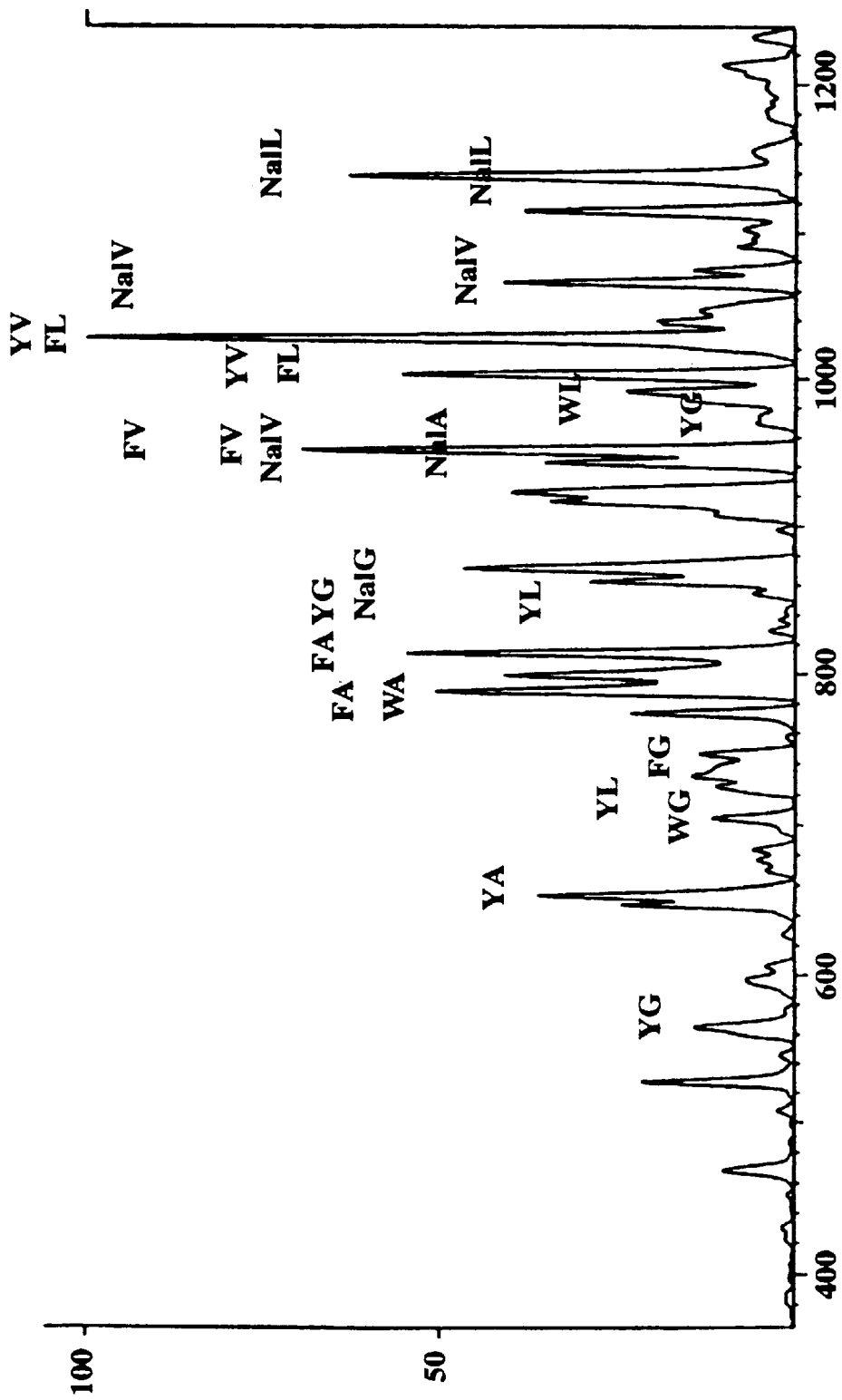
FIG. 7 shows the HPLC chromatogram of a mixture of cyclopentapeptides identified by mass spectrometry (LC-MS). The peptide components are cyclo (Yyy-D-Pro-Asp-Xxx-DLeu), where Xxx=Phe, Tyr, Trp, Nal; Yyy=Gly, Ala, Val, Leu.

Table I contains a listing of the number of cyclic peptides that can be expected if linear peptide mixtures of varying lengths, comprising each of the 20 common amino acids are prepared according to the present invention;

Table II contains a listing of the number of cyclic peptides that can be prepared based on the use of either nineteen (19) or alternatively thirty-eight (38) common L or L,D amino acids, depending on the size of the resulting ring in terms of residue number, and adaptation of the chemistry for the four amino acids (aspartic acid, glutamic acid, asparagine and glutamine) shows the additional numbers of peptide that can be prepared by varying the normally invariant resin-bound amino acid;

Table III contains a listing of the protected amino acids used in Example 3;

Table IV contains a listing of the abbreviations, symbols, and terminology as utilized herein;

Table V describes the theoretical number of cyclic peptides when one position is fixed, assuming 20 common amino acids at the variable positions;

Table VI describes the theoretical number of cyclic peptides when both support-linked amino acid and a turn-inducing amino acid are incorporated within cyclic peptides of varying ring size;

Table VII shows a comparison of theoretical and actual ratios upon amino acid analysis of the cyclic hexapeptide mixture of Example 4.

Table VIII shows a comparison of theoretical and actual ratios upon amino acid analysis of six sublibraries of a stylostatin heptapeptide as described in Example 5.

Table IX shows the results of the biassay of peptide mixtures prepared in Examples 1–5 in anti-HIV and tumor inhibition tests. A positive response was obtained for 3 of the 12 mixtures in one test.

SYNTHESIS OF MIXTURES OF DEFINED COMPOSITION

A general protocol for carrying out the invention and synthesizing a mixture of peptides is described as follows:

A container including a mixture of peptide resin is (1) split into equal parts or fractions, a different activated amino acid is (2) coupled to each of the resin fractions, the reaction in each fraction is monitored to ascertain that it has gone to completion, and the fractions are (3) recombined to form the mixture of peptides which mixture will contain each peptide (i.e., all amino acid sequence combinations) in retrievable and analyzable amounts. a mix. This is done by preparing equimolar mixtures of amine or side chain-bound protected amino acid resins by mixing the proper weights of resins based on their amino acid substitution (meq amino acid/g resin). Mixing can be carried out as a dilute slurry in dimethylformamide (DMF), with vigorous mixing. The equimolarity of the resin mixture can be confirmed by amino acid analysis. For example, Fmoc chemistry can be used with amino acids coupled as active pentafluorophenyl esters (OPFp esters). Other N-α-protecting chemistries (such as Boc), or other carboxyl terminal activation methods (such as HOBt esters, symmetric anhydrides, etc.) can be used.

The resin mixture can be split into equal portions, either by weight, or volumetrically, as a consistent slurry. It is important that the slury be uniformly consistent to insure that each portion of the mixture contains an equal molar amount of peptide resin. The peptide mixtures to be divided can be synthesized manually. However, mixtures of peptides with a combination of constant and variable residues can be made using a combination of automated and manual approaches. Further, a sequence of constant residues can be added on an automated synthesizer. When using an automated synthesizer, resin being produced can be removed at different points during synthesis to obtain a desired mixture. Any mixture produced via automation can then be split into equal portions and the mixed amino acids coupled manually.

IMPROVED CYCLIZATION CHEMISTRY

A key component for the reliable production of cyclic peptide libraries involves the cyclization step. While resin bound cyclizations of peptide sequences have been described, all of these involve individual peptides and most gave relatively modest yields of cyclic products or involved prolonged reaction times. Both of these are significant disadvantages that had to be overcome in order to provide viable cyclic peptide mixtures. In addition it had to be shown that cyclization processes, which are notoriously sequence dependent, and thus considerably more difficult synthetically than driving linear peptide couplings to completion, could be carried out using a variety of potential sequences including all common amino acids.

An important aspect of the present invention involves a new, recently described coupling agent known as HATU (Carpino, et al., *Journal of the Amer. Chem. Soc.*, 1993). This coupling agent, employs an aza-version of the well-known coupling additive, HOBt (not shown); this newer version is known as HOAt. However, it is contemplated that other coupling agents such as disclosed in U.S. Pat. No. 5,166,394 by Breipohl et al, hereby incorporated by reference may be used.

HOAT can then be used (instead of HOBt) to form the aza-equivalent of the peptide condensation agent HBTu; this now results in an improved condensation agent HATU. The improved properties of HATU are documented in Example 3 in which a cyclization step not complete after 12 hours using BOP/HOBt, could be completed in less than one hour using HATU/HOAT. The successful application of this cyclization chemistry to a mixture of peptides containing all common amino acids (except cysteine) is also demonstrated in Example 3 and is additionally supported by the findings of amino acid analysis which showed expected ratios for both resin-bound and cyclic peptide mixtures.

A second, preferred embodiment of the above invention involves the deliberate incorporation of amino acids known to induce cyclization. These include imino acids such as proline or hydroxy proline, or flexible amino acids such as glycine or various pseudopeptides such as Proψ[CH$_2$S-Gly, inserted at one or more position within the initial sequence. Alternatively, the use of the amine attachment strategy to couple the first amino acid to the solid support also provides a method for inducing cyclization as well as for reducing aggregation during peptide synthesis. These methods may be used separately or combined, for example, to include a proline residue within a linear sequence to enhance cyclization even though the peptide was initially attached to the solid support through and amine function.

EXAMPLE I

N-t-Butyloxycarbonyl-L-aspartic acid anhydride (Boc-Asp anydride). To a solution of 23.3 g N-t-butyloxycarbonyl-L-aspartic acid in 150 mL of tetrahydrofuran was added portionwise 20.6 g of N,N-dicyclohexyl-carbodiimide at 0° C. and overnight at room temperature. The precipitated dicyclohexyl urea was filtered off and all solvent was evaporated under reduced pressure. The oily residue was crystallized from acetone/hexane to give 18.24 g of anydride as white needles.

N-t-Butyloxycarbonyl-aspartic acid-α-fluoromethyl ester. To the solution of 11.76 g fluorenyl methanol and 12.90 g N-t-butyloxycarbonyl aspartic acid anhydride in 50 mL of tetrahydrofuran was added 10.2 mL of diisopropylethy-lamine. The reaction mixture was stirred for 2.5 h at room temperature, after which all solvents were evaporated under reduced pressure. The remaining oil was dissolved in 200 mL of ethyl acetate and washed three times each with HCl and saturated NaCl, and then dried over Na$_2$SO$_4$. After evaporation of part of the solvent, the product was crystallized from ethyl acetate/hexane yielding 11.60 g of white crystals of a-ester. [α]$_{D20}$=−24.0 (c=1; MeOH) m.p.=155.5° C.

Attachment of N-t-butyloxycarbonyl aspartic acid α-fluorenylmethyl ester to solid support. To a cooled (0°) suspension of 4.83 hydroxymethyl polystyrene in a solution of 1.97 g tryphenylphosphine in 40 mL of tetrahydrofuran was added dropwise a solution of N-t-butyloxycarbonyl aspartic acid a-fluorenylmethyl ester and diethyl azodiacar-boxylate in THF over 30 min. The reaction mixture was stirred at 0° C. for 1 h and overnight at room tempature. Next the resin was filtered and washed 3 times each with THF, CH$_2$C$_2$, and MeOH and then dried. The hydroxyl groups remaining on the resin were then capped by stirring a suspension of the resin in 50 mL CH$_2$Cl$_2$ with benzoyl chloride (1.65 mL) and pyridine (1.5 mL) for 2 h at 0° C. The resin was again washed 3 times with: CH$_2$Cl$_2$ and MeOH and then dried. Yield: 5.48 g.

The amount of N-t-butyloxycarbonyl aspartic and α-fluoromethyl ester loaded on the resin was estimated by the UV absorbance method as described by Meienhofer el al. (*Int., J. Peptide Protein Res.*, 13, 35, 1979) and gave a substitution value of 0.3 meq/g of resin.

Preparation of peptide mixture Fmoc-X-D-Leu-Val-D-Pro-Asp-(OCH$_2$-resin)-OFm, where X=Ala, Phe, Tyr, Trp. The resin (3.38 g, 1 mmol) containing N-t-butyloxycarbonyl aspartic acid α-fluorenylmethyl ester linked to a polymer via its β-carboxyl group was placed in a reaction vessel of a Synthor automated 2000AT peptide synthesizer and treated as follows:

1. Wash CH$_2$Cl$_2$ (3×2 min)
2. Deprotection of t-Boc group 40% TFA/CH$_2$Cl$_2$ (5 min+25 min)
3. Wash CH$_2$Cl$_2$ (6×2 min)
4. Neutralization 10% DIEA/CH$_2$C$_2$ (2×2 min)
5. Wash CH$_2$Cl$_2$ (6×2 min)
6. Wash DMF (2×2 min)
7. Coupling with 0.615 g (63 mmol) Boc-D-Pro-OH, 1.326 g (3 mmol) benzotriazol-1-yloxy-tris (dimethylamino) phosphonium hexafluorophosphate (BOP), 0.459 g N-hydroxybenzotriazole dissolved in 20 mL of distilled dimethylformamide containing 4.8 eq diisopropylethy-lamine for 1 h.
8. Wash DMF (3×2 min)
9. Wash CH$_2$Cl$_2$ (3×2 min)
10. Test for presence of unreacted free amino groups (Kaiser et al., *Anah Biochem.*, 34, 595–598 (1970)). If the Kaiser test is positive (blue color, presence of amino group) step 7 should be repeated until the test is negative.

The above scheme was also used to couple Boc-valine and Boc-D-leucine. After coupling Boc-D-leucine, the resin was suspended in DMF and divided volumetrically as a consistent slurry into four equal portions and each was placed in a separate reaction vessel and coupled accordingly with one of the following: Fmoc-Ala-OH (0.311 g), Fmoc-Phe (0.387 g), Fmoc-Tyr(But)-OH (0.457 g), Fmoc-Trp-OH (0.426 g) in each case together with BOP (0.442 g), HOBt (0.153 g), and DIEA (0.25 mL) in DMF for each portion of the resin.

After confirmaiton of the absence free amino groups (in case of a positive test, the resin should be recoupled for an extended time or capped with acetylimidazole in CH$_2$Cl$_2$), resins were washed with DMF and mixed together again in a reaction vessel with shaking in DMF for 15 min.

Cyclization of peptide mixture. The mixture of peptide resins were deprotected with 20% piperidine in DMF for 2 and 15 min, washed again with DMF (8×2 min) and cyclized using 0.884 g (2 mmol) of BOP, 0.306 g (2 mmol) of HOBt and 0.68 mL of DIEA in DMF for 24 h. After washing the resin with DMF (3×2 min), the Kaiser test was positive and cyclization was repeated for an additional 24 h with the same reagents. Very faint blue color was obtained with Kaiser reagents after washing of the resin and the reaction was deemed to have been completed.

Cleavage of the peptide mixture from the resin. Dried resin after cyclization (3.3 g) was treated with anhydrous hydrogen fluoride liquid (35 mL) and dimethyl sulfide (2 mL) and anisole (2 mL) as scavengers for 1 h at 0° C. Then hydrogen fluoride and scavengers were evaporated under vacuum. Remaining solid was extracted with diethyl ether (3×40 mL) and peptides were extracted with acetic acid followed by lyophilization. Yield: 400 mg.

Amino acid analysis: Ala 0.97 (1); Pro 5.04 (4); Tyr 0.74 (1); Val 4 00 (4); Leu 4.53 (4); Phe. 1.08 (1).

Results. The peptide mixture was analyzed for its composition using reversed phase HPLC. The chromatogram showed five major peaks which were separated on preparative column for further characterization. The individual compounds were collected and molecular weights established by fast atom bombardment mass spectrometry. All four expected cyclic peptides were observed. In addition, products corresponding to diastereomers were also identified, and were attributable to epimerization during the cyclization step. In example 3 (below), use of an improved coupling reagent is described which effectively reduces this well-known side reaction. The ability to form mixtures of cyclic peptide products using resin-bound cyclization was thus effectively demonstrated.

EXAMPLE II

Preparation of peptide mixture Fmoc-X-D-Leu-Y-D-Pro-Asp (O-CH$_2$-resin)-OFm, where X=Trp, Nal, Tyr(But). Phe and Y=Gly, Ala, Val. Leu The resin (4.21 g. 2.25 mmol) containing N-t-butyloxycarbonyl aspartic acid α-fluorenylmethyel ester was placed in a reaction vessel of a Synthor 2000AT automatic peptide synthesizer and treated as described in Example I. After attachment of Boc-D-Pro-OH, the resin was divided into four equal portions, and each portion was coupled separately with Boc-Gly-OH (0.394 g, 2.75 mmol), Boc-Ala-OH (0.926 g. 2.25 mmol) in each case together with BOT (0.995 g., 2.25 mmol), HOBT (0.334 g 2.25 mmol), and DIEA (0.384 mL) in DMF 6 mL) for each portion of the resin. After confirmation of the absence of free amine groups, the resins were washed and combined together for the next deprotection and coupling with Boc-D-Leu-OH. Then the resin was divided again into four equal portions and coupled separately with Fmoc-Trp-OH, Fmoc-Tyr(But)-OH, Fmoc-Phe-OH, and Fmoc-Nal-OH. After checking the absence of amine groups, resin were washed with DMF, combined together in a reaction vessel and used for subsequent steps involving partial deprotection and resin-bound cyclization.

Cyclization of peptide mixture. The mixture of peptide resins were deprotected with 20% piperidine in DMF for 2 and 15 min, washed again with DMF (8×2 min) and cyclized using 3.97 g of BOP, 1.377 g of HOBt and 3.1 mL of DIEA in DMF (12 mL) for 24 h. After washing the resin with DMF (3×2 min), the Kaiser test was positive and cyclization was repeated for an additional 24 h with the same reagents. Very faint color was obtained with Kaiser reagents after washing of the resin and the reaction was deemed to have been completed.

Amino acid analysis: Asp 4.45 (4); Gly 1.01; Ala 0.98 (1); Pro 3.69 (4); Tyr 0.69 (1); Val. 0.78 (1); Leu 5.00 (5); Phe 1.03 (1); Trp and Nal not estimated.

EXAMPLE III

Synthesis of a Cyclic Pentapeptide cyclo (Aaa-Bbb-Ccc-Ddd-Asp) with 1296 (6×6×6×6) Components. Preparation of peptide mixture, Fmoc-Aaa-Bbb-Ccc-Ddd-Asp (OCH$_2$resin)-OFm, where
Cycle 1: Ddd=Gly, Tyr, Val, Leu, Ser, Glu
Cycle 2: Ccc=Arg, Gly, Trp, Phe, Met, Gln
Cycle 3: Bbb=Lys, Ala, Thr, Phe, Glu, Pro
Cycle 4: Aaa=Ala, Phe, Tyr, Ile, His, Gly The Merrifield resin (2.00 g, 1.00 mmol) containing N-t-butyloxycarbonyl aspartic acid α-fluorenylmethyl ester bound by its side chain through a benzyl ester link to the resin, was divided into six equal portions and coupled accordingly with one of the following amino acids (0.66 mmol each; 4 fold excess); Boc-Gly-OH (0.117 g), Boc-Tyr (Cl$_2$Bzl)(0.293 g), Boc-Val-OH (0.145 g), Boc-Leu-OH (0.166 g), Boc-Ser(Bzl)-OH (0.197 g), Boc-Glue (OChx)-OH 0.219 g) in each case together with BOP (0.295 g), HOBt (0.102 g) and DIEA (0.114 mL) in 6 mL of DMF for each portion of the resin.

After confirmation of the absence of free amino groups (in case of a positive test), the resin should be recoupled for an extended time. The resins were washed with DMF and mixed together again in a reaction vessel with shaking in DMF for 15 min. Following the above, additional cycles 2, 3, and 4 were done in a similar fashion using t-butyloxycarbonyl amino acids (shown in Table III) with proper side protecting group or using N-terminal-protected α-fluorenylmethyloxy-carbonyl amino acids for cycle 4. After completion of cycle 4, the resins were washed with DMF, combined, and again washed with DMF, CH$_2$Cl$_2$, and then dried. Yield: 6.83 g.

Method A. Cyclization using standard coupling reagent. A sample (1.65 g, 0.5 mmol) of peptide mixture resin was deprotected with 20% piperidine in DMF as described in example I and extensively washed with DMF to remove traces of piperidine. Then the resin was cyclized for 24 h with 0.884 g (2 mmol) of BOP, 0.306 g (2 mmol) of HOBt and 0.684 mL of DIEA in 10 mL of DMF. A very faint blue color was obtained with Kaiser ninhydrin reagents after washing of the resin and the reaction was deemed to have been completed.

Amino acid analysis: Asp 6.05 (6); Glue 2.84 (3); Ser 0.67 (1); Gly 3.20 (3); His 0.85 (1); Arg 0.79; Thr 0.76 (1); Ala 1.74 (2); Tyr 1.57 (2); Val 1.05 (1); Met 0.67 (1); Ile 0.85 (1); Leu 1.00 (1); Phe 3.20 (3); Lys 0.63 (1); Trp not estimated.

Cleavage of the peptide mixture from the resin. Dried resin after each cyclization (1.1 g) was treated with anyhrous fluoride liquid (20 mL) and dimethyl sulfide (1 mL) and anisole (1 mL) as scavengers for 1 h at 0° C. Then hydrogen fluoride and scavengers were evaporated under vacuum. Remaining solid was extracted with methyl ether (3×40 mL) and peptides were extracted with 50% acetic acid followed by lyophilization. Yield; 0.255 g.

Amino acid analysis: Asp 6.43 (6); Glu 2.49 (3); Ser 0.67 (1); Gly 3.15 (3); His 1.02 (1); Arg 1.07 (1); Thr 0.79 (1); Ala 2.07 (2); Pro 1.02 (1); Try 1.47 (2); Val 1.00 (1); Met 0.43 (1); Ile 0.53 (1); Leu 1.03 (1); Phe 2.83 (3); Lys 1.1 (1); Trp not estimated.

Method B. Cyclization using HATU (Carpino, 1993). The mixture of the peptide resins (1.65 g, 0.5 mmol) were deprotected with 20% piperidine in DMF for 2 and 15 min washed again extensively with DMF and cyclized using 0.76 g (2 mmol) of HATU, 0.272 g (2 mmol) of HOAT, and 0.684 mL of DIEA in 10 mL of DMF. Cyclization was complete in 1 h based on Kaiser ninhydrin test. The resin was washed with DMF, CH$_2$Cl$_2$, MeOH, Et$_2$O and dried.

Amino acid analysis: Asp 6.61 (6); Glu 3.11 (3); Ser 0.61 (1); Gly .339 (3); His 0.76 (1); Arg 1.00 (1); Thr 0.76 (1); Ala 1.88 (2); Pro 0.87 (1); Tyr 1.83 (2); Val. 0.47 (1); Met 0.76 (1); Ile 0.96 (1); Leu 0.83 (1); Phe 3.43 (3); Lys 0.95 (1); Trp not estimated.

Cleavage from the peptide mixture from the resin. Dried resin after each cyclization (1.1 g) was treated with anhydrous hydrogen fluoride liquid (20 mL) and dimethyl sulfide (1 mL) and anisole (1 mL) as scavengers for 1 h at 0° C. Then hydrogen fluoride and scavengers were evaporated under vacuum. Remaining solid was extracted with methyl ether (3×40 mL and peptides were extracted with 50% acetic acid and followed by lyophilization. Yield: 0.261 g.

Amino acid analysis: Asp 6.47 (6); Glu 2.65 (3); Ser 0.72 (1); Gly 3.74 (3); His 1.22 (1); Arg 1.10 (1); Thr 0.88 (1); Ala 2.13 (2); Pro 1.29 (1); Tyr 1.07 (2); Val 1.00 (1); Met 0.79 (1); Ile 0.91 (1); Leu 1.15 (1); Phe 2.79 (3); Lys 0.69 (1); Trp not estimated.

TABLE VII

RGD-based cyclohexapeptide libraries: results of amino acid analysis for resin-bound (A) and release (B) cyclic peptide mixtures

| SL | L-Ala[1] | | D-Ala[1] | | L-Pro[1] | | D-Pro[1] | | |
|---|---|---|---|---|---|---|---|---|---|
| AA | A | B | A | B | A | B | A | B | Theory |
| Asp | 4.0 | 4.0 | 4.4 | 4.0 | 4.8 | 4.0 | 4.3 | 4.0 | 4 |
| Glu | 3.5 | 3.2 | 3.6 | 3.6 | 4.0 | 3.5 | 3.5 | 3.3 | 4 |
| Gly | 2.3 | 2.4 | 2.2 | 2.2 | 2.0 | 2.2 | 2.0 | 2.0 | 2 |
| Arg | 0.8 | 1.2 | 1.2 | 1.0 | 0.5 | 1.0 | 0.5 | 1.0 | 1 |
| Ala | 3.1 | 2.9 | 3.5 | 3.3 | — | — | — | — | 4 |
| Pro | — | — | — | — | 4.2 | 3.6 | 3.7 | 3.5 | 4 |
| Tyr | 0.7 | 0.6 | 0.71 | 0.7 | 1.3 | 0.6 | 1.1 | 0.6 | 1 |
| Val | 0.7 | 0.8 | 0.94 | 0.8 | 1.1 | 1.0 | 0.9 | 0.9 | 1 |
| Leu | 0.9 | 1.1 | 1.3 | 1.2 | 1.1 | 1.2 | 0.7 | 1.1 | 1 |
| Phe | 4.3 | 4.1 | 5.0 | 4.9 | 5.7 | 4.9 | 5.2 | 4.7 | 5 |
| Trp | n.d. | n.d. | n.d. | n.d. | n.d. | n.d. | n.d. | n.d. | 11 |

TABLE VIII

Stylostatin-Based Cyclopeptide Libraries: Results Amino Acid Analyses for Resin-bound (A) and Release (B) Cyclic Peptide Mixtures

| | SL | | | | | | | | | | | |
|---|---|---|---|---|---|---|---|---|---|---|---|---|
| | L-Tyr[1]- | | D-Tyr[1]- | | L-Ser[1]- | | D-Ser[1]- | | L-Thr[1]- | | D-Thr[1]- | THEO- |
| AA | A | B | A | B | A | B | A | B | A | B | A | B | RY |
| Asp | 4.3 | 3.9 | 5.2 | 3.9 | 4.3 | 3.8 | 4.4 | 4.1 | 5.4 | 4.8 | 5.0 | 4.0 | 4 |
| Ser | — | — | — | — | 0.1 | 3.0 | 1.1 | 3.3 | — | — | — | — | 4 |
| Leu | 1.2 | 1.0 | 0.7 | 1.0 | 0.7 | 1.0 | 0.8 | 1.0 | 1.0 | 1.0 | 1.0 | 1.0 | 1 |
| Phe | 7.0 | 5.5 | 7.6 | 6.0 | 3.6 | 5.1 | 7.8 | 9.3 | 5.8 | 5.8 | + | 5.1 | 5 |
| Ala | 6.8 | 7.3 | 7.7 | 6.8 | 6.0 | 6.8 | 6.9 | 7.0 | 7.2 | 8.4 | 7.9 | 6.8 | 7 |
| Ile | 1.0 | 0.9 | 1.0 | 1.0 | 1.0 | 0.6 | 1.0 | 1.0 | 1.0 | 0.8 | 1.0 | 0.7 | 1 |
| Pro | 4.7 | 5.0 | 5.2 | 4.8 | 4.3 | 4.3 | 5.0 | 4.6 | 4.9 | 5.4 | 5.4 | 4.5 | 4 |
| Tyr | 3.0 | 3.6 | 3.6 | 3.7 | — | — | — | — | — | — | — | — | 4 |
| Thr | — | — | — | — | — | — | — | — | 3.5 | 4.3 | 3.6 | 3.5 | 4 |
| Trp | n.d. | | n.d. | | n.d. | | n.d. | | n.d. | | n.d. | | 1 |

A = resin bound; B = HF cleaved and deprotected
(+) = amino acid present but quantitation unreliable; n.d. = not determined
AA = amino acid
SL = sublibrary (varies according to position 1 substituent)

TABLE IX

NCI Tests Cyclic Peptide Libraries

| NCI No. | Peptide Mixture | In Vitro Anti-HIV $EC_{50}$ | Tumor Inhibition |
|---|---|---|---|
| 900,000 | 4 endothelin antagonists (cyclic pentapeptides | >100 | |
| 900,001 | 16 endothelin antagonists (cyclic pentapeptides) | | |
| 900,002 | 1296 cyclic pentapeptides | $5.56 \times 10^1$ | |
| 900,003 | 16 RGD cyclic hexapeptides (L-Ala) | >100 | |
| 900,004 | 16 RGD cyclic hexapeptides (D-Ala) | $5.18 \times 10^1$ | |
| 900,005 | 16 RGD cyclic hexapeptides (L-Pro) | $2.62 \times 10^1$ | |
| 900,006 | 16 RGD cyclic hexapeptides (D-Pro) | >100 | |
| 900,007 | 256 stylostatin analogs | >100 | |
| 900,008 | 256 stylostatin analogs | >100 | |
| 900,009 | 256 stylostatin analogs | >100 | |
| 900,010 | 256 stylostatin analogs | >100 | |
| 900,011 | 256 stylostatin analogs | >100 | |
| 900,012 | 256 stylostatin analogs | >100 | |

EXAMPLE IV
Synthesis of an RDG-Based Cyclohexapeptide Library with Four Sublibraries (4×16 Peptides) cyclo (Xxx-Gln-Phe-Yyy-Zzz-Asp), where Xxx=1-Ala L-Pro, D-Pro; Yyy=Arg, Gly, Trp, Phe, and Zzz=Gly, Tyr, Val, Leu Cyclic Hexapeptide Library. Boc-Asp (OCH$_2$-resin)-OFm (3.0 g) corresponding to 1.65 mM of the amino acid bound was swollen in CH$_2$Cl$_2$ and deprotected with TFA/CH$_2$Cl$_2$ treatment. After Boc-deprotection the resin TFA salt was split into four equal parts into four separate reaction vessels. Each portion was acylated with the corresponding Boc-protected amino acid using BOP coupling procedure with simultaneous TFA salt neutralization.

1. 0.526 g (3.0 mM) Boc-Gly-OH, preliminary activated for 5 min with 1.326 g (30 mM) BOP, 0.459 (3.0 mM) HOBt-H$_2$O and 1.03 mL (60 mM) DIPEA in 10 mL DMF;
2. the second resin portion was treated with similarly pre-activated 1.321 g (3mM) Boc-Tyr (2.6 diCl-Bzl)-OH;
3. the third resin portion was treated with similarly preactivated 0.652 g (3 mM) Boc-Val-OH;
4. the fourth resin portion was treated with similarly preactivated 0.748 g (3 mM) Boc-Leu-OH.H$_2$O Each preliminary activated Boc-amino acid was added to one part of the resin in a separate reaction vessel, simultaneously 0.1 mL of DIPEA was added to each portion of resin for the amino group liberation.

A parallel Kaiser test used to confirm that the acylation was complete indicated prolonged reaction times, still 0.25 mL of DIPEA added to each reaction vessel. After 6 h, even though the Kaiser test was still slightly positive, the resin portions were recombined, washed and then Boc-deprotected and TFA liberated according to the protocol.

Second cycle. After the Boc-deprotection and base treatment to destroy the resin-bound peptide TFA salt, the resin was split into four equal parts into four separate reaction vessels. Each part of the resin was acylated with the corresponding Boc-amino acid using BOP coupling procedure:
1) 1.29 g (3.0 mM) Boc-Arg(Tos)-OH;
2) 0.53 g (3.0 mM Boc-Gly-OH;
3) 1.0 g (3.0 mM) Boc-Trp(For)-OH;
4) 0.80 g (3.0 mM) Boc-Phe-OH.

After the acylation reactions were completed (according to Kaiser test) the resin portions were recombined, washed and split into two equal portions. One of these was removed for other purposes, the other Boc-deprotected resin portion liberated from TEA salt according to the protocol was submitted for the next coupling cycle.

Third cycle. After Boc-deprotection the TFA-liberated peptide-resin was acylated with Boc-Phe-OH: 0.80 g (3.0 mM); Boc-Phe-OH, 1.33 g (3.0 mM); BOP and 0.46 g (30 mM) HOBt-H$_2$O were dissolved in 8 mL DMF, 1.03 mL (6.0 mM) DIPEA added and after 5 min reaction mixture was added to the resin. After the reaction was completed as testified by negative Kaiser test the resin was washed, treated with TFA/CH$_2$Cl$_2$ and DIPEA neutralized.

Fourth cycle. After the Boc-deprotection and DIPEA treatment to liberate the TFA salt the resin was acylated with Boc-Gln-OH: 0.738 g (30 mM) of Boc-Gln-OH, 1.33 g (3.0 mM) BOP and 0.46 g (3.0 mM) HOBt-H$_2$O were dissolved in 8 mL of DMF, 1.03 mL (60 mM) DIPEA added and after 5 min the reaction mixture was added to the resin. After the coupling reaction was finished the resin was washed and treated with TFA/CH$_2$Cl$_2$ and DIPEA neutralized.

Fifth cycle. The Boc-deprotected and TFA-liberated resin was split into four equal parts into separate reaction vessels. Each portion was reacted with the correspondingly BOP/HOBt-activated Fmoc-amino acid:
1) 0.233 (0.75 mM) Fmoc-Ala-OH, 0.332 g (0.75 mM) BOP and 0.115 g (0.75 mM) HOBt-H$_2$O dissolved in 5 mL DMF, 0.26 mL 91.5 mM) DIPEA added and after 5 min the reaction mixture with preactivated Fmoc-Ala-OH added to the resin;

2) the second resin portion was treated with similarly preactivated 0.233 g (0.75 mM) Fmoc-D-Ala-OH;

3) the third resin portion was treated with similarly preactivated 0.253 g (0.75 mM) Fmoc-Pro-OH; p0 4) the fourth resin fraction was treated with similarly preactivated 0.253 g (0.75 mM) Fmoc-D-Pro-OH.

After the acylation was complete each fraction of the resin received separate treatment. Each portion was washed, Fmoc-and OFm deprotected with 3 portions of 20% piperidine in DMF (3×10 min) and each of the 4 side chain residues linked deprotected linear hexapeptide mixtures (16 components) was independently submitted to cyclization.

Cyclization, cleavage, and deprotection: c(Ala-hexapeptide library). After Fmoc-and OFm deprotection the resin was washed 3×5 mL DMF, 6×5 mL $CH_2Cl_2$, 2×5 mL DMF, 3×5 mL 10% DIPEA/DMF, 3×5 mL DMF. The solution of 0.285 g (0.75 mM) HATU, 0.102 g (0.75 mM) HOAT, 0.26 mL (1.5 mM) DIPEA in 5 mL DMF was added to the above prepared resin. After 15 min, the Kaiser test was negative indicating the cyclization reaction was complete. The polymer material was filtered and washed 3×5 mL DMF, 3×5 mL 10% DIPEA/DMF, 2×5 mL DMF, 6×5 mL $CH_2Cl_2$, 2×5 mL MeOH, 1×5 mL $Et_2O$ and dried. Yield= 0.40 g.

The resin obtained was treated with 5 mL of liquid hydrogen fluoride in the presence of 0.5 mL anixole and 0.2 mL methyl ethyl sulfide for 1 h at RT. After the evaporation of HF the resin was washed: 3×15 mL $EtO_2$, dried and extracted with 20 mL 50% AcOH, extract diluted with water and freeze dried. Yield=0.054 g.

The three remaining fractions were treated in an identical fashion.

c(D-Ala$^1$-hexapeptide library).
a) yield of the peptide resin after cyclization and the resin: Yield=0.3874 g;
b) yield of the cyclopeptide library after cleavage and deprotection: Yield=0.097 g.

C(Pro$^1$hexapeptide library
a) yield of the peptide resin after cyclization on the resin: Yield=0.4083 g;
b) yield of the cyclopeptide library after cleavage and deprotection: Yield=0.0796 g.

C(D-Pro$^1$hexapeptide library)
a) yield of the peptide resin after cyclization on the resin: Yield=0.4051 g;
b) yield of the cyclopeptide library after cleavage and deprotection: Yield=0.0884 g.

The amino acid ratios obtained for the RGD-based cyclic hexapeptide libraries are listed in Table VII. In each case column A represents the resin-bound cyclic peptides while column B reflects amino acid ratios of the deprotected cleaved products.

EXAMPLE V

Synthesis of a Stylostatin Peptide Library with Six Sub-libraries (6×256 Peptides) Boc-Asp-(MBHA-Resin)-OFm To a suspension of 5.0 g (1.8 mmol) of MBHA.HCl resin in 30 ml DMF was added, 0.31 mL 91.8 mmol) DIPEA followed by a solution of 1.48 g (3.6 mmol) Boc-Asp-OFm, 1.59 g (3.6 mmol) BOP, 0.55 g (3.6 mmol) $HOBt.H_2O$ and 1.23 ml (7.2 mmol) DIPEA in 10 ml DMF. After stirring the reaction mixture for 24 h at room temperature the resin was filtered and washed with 2×20 ml DMF, 3×20 ml $CH_2Cl_2$ and dried over $KOH/P_2O_5$. Yield 5.674 g, theory 5.642 g, 0.317 mmol/g.

Spectrophotometric determination of -OFm ester on the resin provided 0.331 mmol/g (103.8% substitution). Quantitative amino acid analysis suggested a lower loading or 0.184 mmol/g (58% substitution). The higher substitution amount was utilized for purposes of calculating reagent excess.

Stylostatin Library (Stylostatin is cyclo (Leu-Ala-Ile-Pro-Phe-Asn-Ser)) Box-Asp(MBHA-resin)-OFm (5.1 g) corresponding to 1.62 mM of the amino acid bound was swollen in $CH_2Cl_2$ in an hour-glass reaction vessel and treated with TFA/$CH_2Cl_2$ treatment.

After deprotection and liberation from the TFA salt (DIEA wash), the resin was split into four equal parts with four separate reaction vessels (vials). Each portion was acylated with the corresponding Boc-protected amino acid pentafluorophenyl ester (Box-Xxx-OPFP);
1) 0.69 g (1.62 mM) Boc-Phe-OPFP;
2) 0.69 g (1.62 mM) Boc-D-Phe-OPFP;
3) 0.575 g (1.62 mM) Boc-Ala-OPFP; and
4) 0.575 g (1.62 mM) Boc-D-Ala-OPFP.

Each active ester was dissolved in 5 ml of DMF and 1–3 drops of a 1% solution of bromophenol blue (BPB) in ethanol as an indicator was added to the solution for each resin portion. As the reaction proceeded, the color of the suspension turned from blue to yellow; usually the acylation was complete within 5–15 min. depending on the amino acid.

A parallel Kaiser test (32) was used to confirm that the acylation was complete. After the reactions, the resin portions were recombined, washed, and then Boc-deprotected and TFA liberated according to the general protocol.

Second cycle. After Boc-deprotection, the TFA-liberated resin was acylated with Boc-Pro-OPFP; 2.47 g (6.48 mM) Boc-Pro-OPFP was dissolved in 15 ml DMF and added to the resin in the presence of 1 drop of 1% solution of BPB in EtOH. The indicator suggested that within 20 min, the coupling reaction was finished. After the reaction was completed the resin was washed and treated with acid followed by a base neutralization.

Third cycle. After the Boc-deprotection and base treatment, TFA salt, the resin was split into four equal parts in four separate reaction vessels. Each part of the resin was acylated with the corresponding OPFP esters:
1) 0.643 g (1.62 mM) Boc-Ile-OPFP
2) 0.575 g (1.62 mM) Boc-Ala-OPFP
3) 0.575 g (1.62 mM) Boc-D-Ala-OPFP
4) 0.621 g (1.62 mM) Boc-Val-OPFP.

Each one of the active esters was dissolved in 5 ml DMF and added to the separate resin portion with occasional stirring. According to the BPB indicator, complete coupling of the Boc-Leu required 60 min and was the longest coupling; L-Boc-Val was the second longest. After all reactions were judged complete, the resins were mixed, washed, Boc-deprotected and liberated from TFA salt in preparation for next coupling cycle.

Fourth cycle. The Boc-deprotected and TFA-liberated resin was split into four reaction vessels. Each part of the resin was acylated with one of the following -OPFP esters:
1) 0.575 g (1.62 mM) Boc-Ala-OPFP;
2) 0.575 g (1.62 mM) Boc-D-Ala-OPFP;
3) 0.698 g (1.62 mM) Boc-Phe-OPFP;
4) 0.698 g (1.62 mM) Boc-D-Phe-OPFP.

Each one of the active esters were dissolved in 5 ml DMF and added to the separate resin portion with occasional stirring. After the reactions were completed the resin portions were mixed, washed, Boc-deprotected and liberated from the TFA salt according to the protocol for the next coupling cycle.

Fifth cycle. The Boc-deprotected and TFA-liberated resin was split into four equal parts in four separate reaction vessels. Each part of the resin was acylated with the corresponding -OPFP ester:
1) 0.643 g (1.62 mM) Boc-Leu-OPFP;
2) 0.698 g (1.62 mM) Boc-Phe-OPFP;
3) 0.807 (1.62 mM) Boc-Trp(For)-OPFP;
4) 0.575 (1.62 mM) Boc-Ala-OPFP.

Each one of the active esters was dissolved in 5 ml DMF and added to the separate resin portion with occasional stirring. After the reactions were completed the resin was mixed, washed, Boc-deprotected and liberated from the TFA salt according to thep protocol for the next coupling cycle.

Sixth cycle. The Boc-deprotected and TFA liberated resin was split into six equal parts into six separate reaction vessels. Each portion was reacted with the corresponding acylating agent:
1) 0.442 g (1.08 mM) Fmoc-Ser(tBu)-N-carboxy-anydride;
2) 0.593 g (108 mM) Fmoc-D-Ser(tBu)-OPFP;
3) 0.608 g (1.08 mM) Fmoc-Thr(tBu)-OPFP;
4) 0.608 g (1.08 mM) Fmoc-D-Thr(tBu)-OPFP;
5) 0.675 (1.08 mM) Fmoc-Tyr(tBu)-OPFP;
6) 0.675 (1.08 mM) Fmoc-D-Tyr(tBu)-OPFP.

Each one of the activated compounds was dissolved in 5 ml DMF and added to the separate resin portion under occasional stirring. BPB indicated the presence of complete coupling in all reaction vessels within 60 min.

After the reaction each portion of the resin received separate treatment. Each portion was washed, Fmoc- and OFm deprotected with 6 portions of 20% piperidine in DMF (20 min) and each of the 6 side chain residue linked deprotected linear heptapeptide mixtures (256 components) was independently submitted to cyclization.

Cyclization: (L-Tyr$^1$-Stylostatin Library). After Fmoc- and OFm deprotection, the resin was washed in 3×20 ml DMF, 5×20 ml CH$_2$Cl$_2$, 2×20 ml DMF,. 2×20 10% DIPEA/ DMF, 3×20 ml DMF. The solution of 0.411 g (1.08 mM) HATU, 0.147 g (1.08 mM) HOAT, 0.37 ml (2.16 mM) DIPEA in 4 ml DMF was added to the above prepared resin and allowed to run for 2 h with occasional stirring. After 1 h a Kaiser test was negative indicating the cyclization reaction was complete.

The polymer material was filtered and washed with 3×20 ml DMF, 3×20 ml 10% DIPEA/DMF, 2×20 ml DMF, 6×20 ml CH$_2$Cl$_2$, 3×20 ml MeOH, 3×20 ml Et$_2$O, 3×20 ml hexane and dried. Yield: 0.877 g.

The resin (0.614 g, 70% of the material obtained) was treated with 7 ml liquid hydrogen fluoride in the presence of 0.6 ml anisole and 0.2 ml methyl ethyl sulfide for 1 h at RT. After the evaporation of the HF the resin was washed with 3×30 ml Et$_2$O, dried and extracted with 2×20 ml 50% AcOH, extracts diluted with 40 ml H$_2$O and freeze dried. Yield: 0.111 g.

The five remaining portions were treated in an identical fashion:

D-Tyr$^1$-Stylostatin Library:
a) Yield of the peptide resin after cyclization on the resin: Yield: 0.938 g
b) Yield of the cyclopeptide library after cleavage and deprotection: Yield 0.1438 g.

L-Ser$^1$-Stylostatin Library:
a) Yield of the peptide resin after cyclization on the resin: Yield: 0.950 g
b) Yield of the cyclopeptide library after cleavage and deprotection: Yield: 0.130 g.

D-Ser$^1$-Stylostatin Library:
a) Yield of the peptide resin after cyclization on the resin: Yield 1.023 g.
b) Yield of the cyclopeptide library after cleavage and deprotection: Yield: 0.152 g.

L-Thr$^1$-Stylostatin Library:
a) Yield of the peptide resin after cyclization on the resin: Yield 0.946 g.
b) Yield of the cyclopeptide library after cleavage and deprotection: Yield: 0.129 g.

D-Thr$^1$-Stylostatin Library:
a) Yield of the peptide resin after cyclization on the resin: Yield 1.035 g.
b) Yield of the cyclopeptide library after cleavage and deprotection: Yield: 0.132 g.

The amino acid ratios obtained for the stylostatin sub-libraries are listed in Table VIII; in each case, column A represents the resin-bound cyclic peptides while column B reflects amino acid ratios of the deprotected cleaved products. In aggregate the ratios are reasonable for these complex cyclic peptide mixtures.

EXPERIMENTAL ANALYSIS

The peptide mixtures for all the experiments were characterized by quantitative amino acid analysis to verify that the expected amino acids were present in the expected ratios.

Further characterization of the mixtures involved liquid chromatography, capillary electrophoresis, and a variety of mass spectrometric procedures to establish that multiple products were present in reasonably equimolar quantities.

The cyclic peptide mixtures that have been synthesized are unique in representing the first examples of cyclic peptides shown to be preparable in combination and with all coupling reactions driven to completion in spite of the unprecedented diversity of structures present. Heretofore, there have been no literature examples of successful couplings of such mixtures; indeed most cyclization reactions are usually deemed to represent unique challenges, often involving optimized chemistries in each case to obtain acceptable results. The successful resolution of this problem, and the rationale for this disclosure, are largely related to the twin elements of a) resin-bound head-to-tail peptide cyclizations, and b) use of recently described improved coupling agents applied to the cyclization reaction.

The application of the cylic peptide library method to the search for new lead "state of the art" structures in pharmaceutical research or for enzymes inhibitors as receptor antagonists is exemplified by Examples I and III. Example I, a mixture of four new cyclic peptides were prepared, one of which formally corresponds to a known cyclic pentapeptide sequence, described in 1991 (Ihara et al., 1991), as an endothelin antagonist. One of the mixture of four compounds corresponds to a retro-enantio version of the known "Ihara" compound. The other three compounds correspond to a single residue variants of the retro-enantio structure that may be more or less active and these may be tested individually or in combination to simplify the search for a new bioactive lead compound.

In the 1296 cyclic peptides comprising the products of Example 3, the diverse structures were purposely chosen for complexity in order to test the concept using virtually all of the common amino acids. Within this diversity were included 36 compounds that were designed to contain the unique sequence of amino acids known as RGD or Arg-Gly-Asp. This sequence corresponds to a well-known cell adhesion factor. Therefore, this mixture contains numerous molecules known to possess this specific biological activity. By screening with antibodies unique to this sequence, these compounds can be identified. Alternatively, by screening the cyclic peptides for this activity either in solution, or while attached to the original support, new candidate structures with similar or improved RGD-like activity may be identified.

The preferred embodiment of a method for preparing cyclic peptide libraries is shown in examples 1–5. These involve standard Merrifield solid supports, the Boc method of peptide synthesis, cyclization with Bop, HPTU, or the aza derivative of HBTU (known as HATU) (Carpino, 1993), followed by cleavage with anhydrous hydrogen fluoride.

However, other variants of the method are also possible. For example, the initial attachment of the amino acid can be via a carboxylic acid function (either aspartic acid or glutamic acid). But by adding the initial side carboxylic acid function to the well-known benzhydrylamine (BHA) or para-methylbenzhydrylamine (MBHA) functions, the final libraries will now contain the amidated amino acids, asparagine and glutamine. Clearly other trifunctional amino acids with varying structures and chirality may be used to give their corresponding acid or amide functions.

Additionally, the initial amino acid attachment may be accomplished using other side chain functionalities such as alcohols, ethers, thioethers, or amines. For example, the amino acid lysine may be attached to the solid support by an acid-labile urethane linkage with appropriate orthogonal protection.

Other amine-containing amino acids such as ornithine or diaminobutyric acid can be similarly used. By using benzyl linkages, the amino acids serine, threonine, or other hydroxy amino acids can also be ligated to the solid support by their side chains, while the thiol amino acid cysteine can be attached via a thiobenzylether linkage (removable by strong acid or by sodium in liquid ammonia).

A particularly novel feature of this invention involves initial attachment of the first amino acid to the solid support through its amine group. This improvement effectively eliminates the major disadvantage of side chain coupled amino acids in that virtually all amino acids, including a-amino acids, 6-amino acids, and a wide variety of other unusual amino acids, synthetic or naturally occurring, may be used to attach the first amino acid to the solid support. By using a linking agent that is readily cleaved at the end of the synthesis, the cyclized products are released in a unmodified form.

The type of solid support that can be used and the corresponding cleavage procedures (if final cleavage is desired) can also be varied. Among the solid phase resins that can be used are polystyrene resins, polystyrene/polyethylene glycol copolymer supports, polyamides, membrane based solid supports, or other commonly used carriers for peptide synthesis.

The orthogonal protecting groups in the preferred embodiment include the acid-labile Boc group for the amine group (used for repetitive chain elongation) and the base-labile fluorenylmethyloxycarbonyl group used for C-terminal carboxylic acid protection, and strong-acid labile (primarily benzyl) side chain protecting groups. Allyl protection is a particularly convenient method for mild removal, and is utilized for carboxyl protection in the case of attachment of the initial amino acid to the solid support by means of an acid cleavable amine linkage.

Other variants are possible. For example, a variety of other protecting groups are routinely used in peptide synthesis that are cleavable by other means. These provide additional examples of orthogonal protection that can further extend the utility of this method. Specific examples include the ortho-nitroveratryloxycarbonyl (NVOC) amine protecting group (removable by photolysis), the allyloxycarbonyl protecting group (removable by palladium) the Ddz group (removable by hydrazine), or p-nitrosulfenyl group (removable by nucleophilic attack).

The preferred embodiment of preparing cyclic peptides uses a single type of resin-bound linkage to furnish a homogeneous set of cyclic peptide mixtures. However, by using standard techniques of peptide chemistry (and appended by reference to this application—for examples, see Kerr et al., 1993; Lebl et al., 22nd European Peptide Symposium, 1993), it is possible to cleave a portion of the peptide from the resin using one set of chemistries while leaving a second and third component intact for a second round of bioassays or for structure elucidation.

The following detail description is given primarily for clearness of understanding and no unnecessary limitations are to be understood therefrom, for modifications will become obvious to those skilled in the art based upon more recent disclosures and may be made without departing from the spirit of the invention and scope of the appended claims.

We claim:

1. A method of synthesizing and screening cyclic peptide libraries having individual components consisting of from four to twelve amino acid residues and including at least one tri-functional amino acid and utilizing specified chemical synthesis of cyclic peptide mixtures using side chain attachment and head to tail cyclization for preparing a mixture of cyclic peptides of known composition containing cyclic peptides with a specified sequence portion for determining activity of said cyclic peptide in solution with an acceptor molecule of interest comprising the steps of:

a) attaching a specific tri-functional amino acid having an amino terminus, a carboxyl terminus, and at least one side chain, to a solid resin support wherein said side chain of said amino acid is covalently attached to said resin support and protecting said amino terminus or said carboxyl terminus with at least one individually removable protecting group;

b) dividing an amino acid mixture into a plurality of amino acid pools, each of said amino acid pools containing an equal molar amount of said amino acid mixture;

c) coupling a different single selected amino acid to said resin-linked amino acid mixture in each of said pools, said selected amino acid being selected from a group consisting of single orthogonally protected amino acids producing a dipeptide;

d) recombining said dipeptide with said amino acid mixture in each of said pools creating a complex peptide mixture containing said selected amino acids forming a plurality of known peptide chain compositions in a retrievable and analyzable amount;

e) repeating steps b–d with sequential cleaving, dividing, and coupling steps forming a peptide of specified length;

f) subjecting said complex peptide mixture to specific reagents liberating a single amino group and a single carboxyl group in each of said peptide chain compositions forming a plurality of resin-bound compounds;

g) treating said resin-bound compounds supporting said peptide chain compositions with a selected condensation reagent forming a reaction therebetween, and driving said reaction to completion forming cyclic peptides on said resin;

h) detaching said cyclic peptides from said solid resin support by means of a cleaving reagent forming cyclic peptide libraries in solution; and i) performing biological and/or analytical assays on said cyclic peptide libraries in solution for determining activity of said cyclic peptides with said acceptor molecule of interest.

2. The method of claim 1, including the step of subjecting said cyclic peptides in solution to at least one analytical and/or biological assay, establishing the fidelity of the synthetic transformations, and assessing whether the collective mixture of said cyclic peptides has at least one specified biological property by screening said cyclic peptides collectively or in smaller groups against tests with specific antibodies or bioassays for detecting cyclic peptides having reactions to said tests.

3. The method of claim 2, further including the step of identifying cyclic peptides having reactions to said tests by establishing an iterative technique of resynthesis and reassay of progressively smaller groups of said collective mixture.

4. The method of claim 1, whereby the initial amino acid attachment is to a resin preconstructed to provide at least two orthogonally cleavable linkages, said linkages being sequentially cleavable using a combination of photolysis and a strong acid or base treatment, thereby releasing said cyclic peptide mixtures in sequence producing at least one sub-library fraction of cyclic peptide mixtures having similar characteristics for bioassay or chemical analysis.

5. The method of claim 1, wherein said cleaving agents are selected from the group consisting of a strong acid, an anhydrous hydrogen fluoride, an ammonolysis, a nucleophilic displacement, a photolysis, a hydrogenolysis, an electrolysis, a strong base, and a redox process.

6. The method of claim 1, wherein said individually removable protecting groups are selected from the group consisting of acid cleavable groups, base cleavable groups, groups cleavable by transition metals, photolysis, ammonia, thiols, and hydrazines.

7. The method of claim 1, wherein said peptide-resin mixture comprises peptides ranging from about four to about twelve amino acid residue, linked through said at least one amino terminus or said at least one carboxyl terminus, of one of the amino acids.

8. The method as recited in claim 1, wherein said different single orthogonally protected amino acid is selected from the group consisting of L-amino acids, D-amino acids, synthetic amino acids, at least one backbone modified pseudodipeptide and peptide isostere structure.

9. The method as recited in claim 1, wherein said selected condensation reagent is selected from the group consisting of dicyclohexylcarbodiimide active esters, symmetric anhydrides, BOP or other phosphonium reagents, DPPA and other azide reagents, HBTU, and TBTU, or other uranium reagents in combination or without addition of racemization suppressing additives including HOBt or HABt.

10. The method as recited in claim 1, wherein detaching said peptide from said solid support is by treatment with a strong acid, a strong base, photolysis, phase transfer catalysis, or catalytic transfer hydrogenation.

11. A method of synthesizing and screening cyclic peptide libraries having individual components consisting of from four to twelve amino acid residues and including a tri-functional amino acid and utilizing specified chemical synthesis of cyclic peptide mixtures using side chain attachment and head to tail cyclization for preparing a mixture of cyclic peptides of known composition containing cyclic peptides with a specified sequence portion for determining activity of said cyclic peptide in solution with an acceptor molecule of interest comprising the steps of:

a) attaching at least one specific tri-functional amino group having an amino terminus, a carboxyl terminus, and at least one side chain, to a solid resin support wherein said side chain of said amino acid is covalently attached to said resin support and protecting said amino terminus or said carboxyl terminus with at least one individually removable protecting group;

b) linking a trifunctional amino acid residue having a carboxyl or carboxamide linkage to said solid resin support through a Beta-carboxylic function;

c) protecting said trifunctional amino acid residue by attachment of a fluorenylmethyl ester on the Alpha-carboxylic group and attachment of a Boc or Fmoc on the N-terminal amino function;

d) removing the Boc or Fmoc protecting group on the N-terminal amine group with TFA or piperidine;

e) selectively deprotecting the C-terminal carboxyl group of the trifunctional amino acid residue cleaving the C-terminal ester with piperidine;

f) adding HATU reagent for resin-bound cyclizing action with or without HABt providing for end-to-end cyclization;

g) deprotecting the amino and carboxyl termini and other side chain protected functions of the side chains of the trifunctional residues with a selected condensation reagent consisting of a strong acid forming a reaction therebetween, and driving said reaction to completion forming a cyclic peptide on said resin;

h) cleaving said cyclic peptide from the resin with a cleaving reagent consisting of a strong acids i) producing a mixture of cyclic peptide libraries in solution with a fixed amino acid residue at a single position; and j) performing biological and/or analytical assays on said cyclic peptide libraries in solution for determining activity of said cyclic peptides with an acceptor molecule of interest.

12. The method recited in claim 11, including the step of modifying the initial linkage using a basic diamino acid and preparing a variety of cyclic peptides with at least one basic residue in the sequence.

13. The method recited in claim 12, wherein said basic diamino acid is selected from the group consisting of lysine, ornithine, and diaminobutyric acid.

14. The method recited in claim 11, including the step of modifying the initial linkage by linking hydroxy containing amino acids containing at least one hydroxyl function using a cleavable ether linkage.

15. The method recited in claim 11, wherein said trifunctional amino acid is selected from the group consisting of lysine, ornithine, serine, threonine, aspartic acid, glutamine, and glutamic acid.

16. The method recited in claim 1, whereby at least one pair of amino acids in the cyclic peptide structure is substituted by at least one modified peptide prolonging biological half-lives of said cyclic peptides by retarding or preventing enzyme degradation.

17. The method recited in claim 11, including cleaving said cyclic peptide from said solid resin support using a strong acid, a strong base, photolysis, a phase transfer catalysis, catalytic transfer hydrogenation, or ammonolysis.

18. A method of synthesizing and screening cyclic peptide libraries having individual components consisting of from four to twelve amino acid residues and including a tri-functional amino acid and utilizing specified chemical synthesis of cyclic peptide mixtures using side chain attachment and head to tail cyclization for preparing a mixture of cyclic peptides of known composition containing cyclic peptides with a specified desired sequence portion for determining activity of said cyclic peptides in solution with an acceptor molecule of interest comprising the steps of:

a) attaching a specific trifunctional amino group having a side chain including an N-terminal amino acid and a terminal carboxyl group to a selected solid support resin wherein said side chain of said amino acid is covalently attached to said resin support while said amino and carboxyl termini are protected with individually removable protecting groups;

b) providing a given amount of a mixture of amino acid or selected peptide-derivatized resins forming a peptide-resin mixture;

c) dividing said peptide-resin mixture into a number of pools, each of said pools containing an equal molar amount of said peptide-resin mixture;

d) coupling a different single orthogonally protected activated amino acid to said peptide-resin mixture in each of said pools forming a plurality of peptide pool mixtures;

e) recombining said peptide pool mixtures forming a complex peptide-resin mixture of known composition containing each peptide in a retrievable and analyzable amount containing substantially equal molar amounts of each of said peptides;

f) repeating steps (a–d) forming a resin-bound peptide having at least one peptide chain of the desired length attached to said selected solid support resin;

g) subjecting the complex peptide-resin mixture to specific reaction conditions for removing said protecting groups and liberating a single amino group and a single carboxyl group in each peptide chain;

h) treating said resin-bound peptide with an appropriate condensation reagent driving the reaction to completion cyclizing said resin-bound peptide chain forming a new amide bond linking said single amino group and said single carboxyl group forming a resin-bound cyclic peptide with a sequence unique for each resin particle;

i) detaching said cyclic peptide from said resin solid support by means of a cleaving reagent consisting of a strong acid, producing a mixture of cyclic peptide libraries in solution with a fixed amino acid residue at a single position; and j) performing biological and/or analytical assays on said cyclic peptide libraries in solution for determining activity of said cyclic peptides with said acceptor molecule of interest.

19. A method of synthesizing and screening cyclic peptide libraries having individual components consisting of from four to twelve amino acid residues and including a trifunctional amino acid and utilizing specified chemical synthesis of cyclic peptide mixtures using side chain attachment and head to tail cyclization for preparing a mixture of cyclic peptides of known composition containing cyclic peptides with a specified sequence portion for determining activity of said cyclic peptide in solution with an acceptor molecule of interest comprising the steps of:

a) attaching a specific trifunctional amino group having a side chain including an N-terminal amino acid and terminal carboxyl group to a selected solid support resin wherein said side chain of said amino acid is covalently attached to said resin support while said amino and carboxyl termini are protected with individually removable protecting groups;

b) providing a given amount of a mixture of amino acid or selected peptide-derivatized resins forming a peptide-resin mixture;

c) dividing said peptide-resin mixture into a number of pools, each of said pools containing an equal molar amount of said peptide-resin mixture;

d) coupling a different single orthogonally protected activated amino acid to said peptide-resin mixture in each of said pools forming a plurality of peptide pool mixtures;

e) recombining said peptide pool mixtures forming a complex peptide-resin mixture of known composition containing each peptide in a retrievable and analyzable amount containing substantially equal molar amounts of each of said peptides;

f) repeating steps (a–e) forming a resin-bound peptide having at least one peptide chain of the length attached to said selected resin;

g) subjecting the complex peptide-resin mixture to specific reaction conditions for removing said protecting groups and liberating a single amino group and a single carboxyl group in each peptide chain;

h) treating said resin-bound peptide with an appropriate condensation reagent driving the reaction to completion cyclizing said resin-bound peptide chain forming a new amide bond linking said single amino group and said single carboxyl group forming a resin-bound cyclic peptide with a sequence unique for each resin particle;

i) detaching said resin-bound cyclic peptide from said solid support resin by means of a cleaving reagent forming cyclic peptide libraries in solution;

i) subjecting said cyclic peptide libraries to various analytical and biological assays establishing the fidelity of the synthetic transformations assessing whether the collective mixture of cyclic peptides has at least one biological property;

j) determining if subsets of the pools are found to possess activities with said acceptor molecule of interest; and k) identifying the positively-responding agents by an iterative technique of resynthesis and reassay of smaller groups.

20. The method of claim 2, including the step of identifying problem cyclization sequences by subjecting resin bound peptides found to be resistant to normal cyclization procedures to identification tests after identifying beads containing such resistant sequences by appropriate chemical or biological tests thereby enabling the rapid screening of a multitude of sequences.

21. The method recited in claim 2 wherein said different single orthogonally protected amino acid is selected from the group consisting of L-amino acids, D-amino acids, synthetic amino acids, and modified peptides.

22. The method recited in claim 11, wherein said amino acid is selected from the group consisting of L-amino acids, D-amino acids, synthetic amino acids, and modified peptides.

23. The method recited in claim 18, wherein said amino acid is selected from the group consisting of L-amino acids, D-amino acids, synthetic amino acids, and modified peptides.

24. The method recited in claim 19, wherein said amino acid is selected from the group consisting of L-amino acids, D-amino acids, synthetic amino acids, and modified peptides.

* * * * *